United States Patent
Bang et al.

(10) Patent No.: US 8,988,438 B2
(45) Date of Patent: Mar. 24, 2015

(54) MOTION CAPTURE APPARATUS AND METHOD

(75) Inventors: Won-chul Bang, Seongnam-si (KR); Hyong-euk Lee, Yonging-si (KR)

(73) Assignee: Samsung Electronics Co., Ltd., Suwon-si (KR)

(*) Notice: Subject to any disclaimer, the term of this patent is extended or adjusted under 35 U.S.C. 154(b) by 1519 days.

(21) Appl. No.: 12/458,103

(22) Filed: Jun. 30, 2009

(65) Prior Publication Data
US 2009/0322763 A1    Dec. 31, 2009

(30) Foreign Application Priority Data
Jun. 30, 2008 (KR) .................. 10-2008-0062837

(51) Int. Cl.
| | | |
|---|---|---|
| G06T 13/00 | (2011.01) | |
| G06T 13/20 | (2011.01) | |
| G06F 3/01 | (2006.01) | |
| G06K 9/00 | (2006.01) | |
| A61B 5/11 | (2006.01) | |

(52) U.S. Cl.
CPC ............ G06F 3/011 (2013.01); G06K 9/00342 (2013.01); *A63F 2300/105* (2013.01); *A63F 2300/6607* (2013.01); *A61B 5/1116* (2013.01); *A61B 5/1121* (2013.01)
USPC ............................ 345/474; 345/420; 345/473

(58) Field of Classification Search
USPC .................. 345/473, 474, 420, 592
See application file for complete search history.

(56) References Cited

U.S. PATENT DOCUMENTS

| | | | |
|---|---|---|---|
| 5,744,953 A * | 4/1998 | Hansen ................... | 324/207.17 |
| 5,990,908 A | 11/1999 | Thingvold | |
| 6,148,280 A * | 11/2000 | Kramer ................... | 702/153 |
| 6,820,025 B2 * | 11/2004 | Bachmann et al. ........ | 702/94 |
| 7,403,202 B1 * | 7/2008 | Nash ..................... | 345/474 |
| 7,489,806 B2 * | 2/2009 | Mohri et al. ............. | 382/107 |
| 8,013,852 B2 | 9/2011 | Ng-Thow-Hing et al. | |
| 8,165,844 B2 | 4/2012 | Luinge et al. | |
| 8,355,529 B2 | 1/2013 | Wu et al. | |
| 2003/0215130 A1 | 11/2003 | Nakamura et al. | |

(Continued)

FOREIGN PATENT DOCUMENTS

| | | |
|---|---|---|
| EP | 1870038 | 12/2007 |
| JP | 08-221599 | 8/1996 |

(Continued)

OTHER PUBLICATIONS

H.J. Luinge (Thesis: "Inertial Sensing of Human Movement"), 2002, Twente University Press.*

(Continued)

*Primary Examiner* — Kimbinh T Nguyen
(74) *Attorney, Agent, or Firm* — NSIP Law

(57) ABSTRACT

Provided are an apparatus and a method of effectively creating real-time movements of a three dimensional virtual character by use of a small number of sensors. More specifically, the motion capture method, which maps movements of a human body into a skeleton model to generate movements of a three-dimensional (3D) virtual character, includes measuring a distance between a portion of a human body to which a measurement sensor is positioned and a reference position and rotation angles of the portion, and estimating relative rotation angles and position coordinates of each portion of the human body by use of the measured distance and rotation angles.

59 Claims, 20 Drawing Sheets

(56) References Cited

U.S. PATENT DOCUMENTS

| | | | |
|---|---|---|---|
| 2008/0112592 A1 | 5/2008 | Wu et al. | |
| 2008/0211808 A1 | 9/2008 | David et al. | |
| 2008/0278497 A1* | 11/2008 | Jammes et al. | 345/474 |
| 2008/0285805 A1* | 11/2008 | Luinge et al. | 382/107 |
| 2009/0322763 A1* | 12/2009 | Bang et al. | 345/474 |

FOREIGN PATENT DOCUMENTS

| | | |
|---|---|---|
| JP | 09-138863 | 5/1997 |
| JP | 09-330424 | 12/1997 |
| JP | 10-021424 | 1/1998 |
| JP | 10-154238 | 6/1998 |
| JP | 10-261090 | 9/1998 |
| JP | 2003-308532 | 10/2003 |
| JP | 2004-157850 | 6/2004 |
| JP | 2005-535031 | 11/2005 |
| JP | 2006-020780 | 1/2006 |
| JP | 2006-034343 | 2/2006 |
| JP | 2006-343114 | 12/2006 |
| JP | 2007-333690 | 12/2007 |
| JP | 2008-533459 | 8/2008 |
| JP | 2008-289866 | 12/2008 |
| JP | 2010-088628 | 4/2010 |
| KR | 1020070120443 | 12/2007 |
| WO | WO 2007/058526 | 5/2007 |
| WO | WO 2008/026357 | 3/2008 |

OTHER PUBLICATIONS

Saint-Bauzel, Ludovic et al., "Real-time Human Posture Observation from a Small Number of Joint Measurements," Proceedings of the 2007 IEEE/RSJ International Conference on Intelligent Robots and Systems San Diego, CA, USA, Oct. 29-Nov. 2, 2007, pp. 3956-3961.

Ukida, Hiroyuki et al., "Human Motion Capture System Using Color Markers and Silhouette", IMTC 2006—Intstrumentation and Measurement Technology Conference Sorrento, Italy Apr. 24-27, 2006; pp. 151-156.

Luinge, H.J., "Inertial Sensing of Human Movement," Twente University Press, P.O. Box 217,7500 AE Enschede, the Netherlands, www.tup.utwente.nl, Copyright 2002 pp. 1-87.

D. Roetenberg et al., "Ambulatory Position and Orientation tracking Fusing Magnetic and Inertial Sensing", IEEE Transactions on Biomedical Engineering, vol. 54, No. 5, May 2007, pp. 883-pp. 890.

D. Vlasic et al., "Practical Motion Capture in Everyday Surroundings", ACM Transactions on Graphics, vol. 26, No. 5, Article 35, Jul. 2007, pp. 35-1-pp. 35-10.

H. Junker et al., "Gesture spotting with body-worn inertial sensors to detect user activities", Pattern Recognition, Elsevier, vol. 41, No. 6, Jun. 2008, pp. 2010-pp. 2024.

M. Brodie et al., "Fusion motion capture: a prototype system using inertial measurement units and GPS for the biomechanical analysis of ski racing", Sports Technology, vol. 1, No. 1, Jun. 25, 2008, pp. 17-pp. 28.

D. Roetenberg, Inertial and Magnetic Sensing of Human Motion, PhD Thesis, XP055044540, May 24, 2006, pp. 1-pp. 126.

H.J. Luinge et al., "Ambulatory measurement of arm orientation", Journal of Biomechanics, vol. 40, No. 1, Dec. 5, 2006, pp. 78-pp. 85.

Japanese Office Action dated Feb. 4, 2014 from Japanese Patent Application No. 2009-155856, 23 pages.

Extended European Search Report dated Jan. 7, 2014 from European Patent Application No. 09164139.9, 8 pages.

* cited by examiner

MOTION CAPTURE APPARATUS AND METHOD

CROSS-REFERENCE TO RELATED APPLICATIONS

This application claims the benefit under 35 U.S.C. §119(a) of Korean Patent Application No. 10-2008-0062837, filed on Jun. 30, 2008, the disclosure of which is incorporated herein in its entirety by reference.

BACKGROUND

1. Field

One or more embodiments relate to a motion capture apparatus and method, and more particularly, to an apparatus and method for generating real-time motion for a three dimensional (3D) virtual character with a minimized number of sensors.

2. Description of the Related Art

As various types of game consoles have been widely distributed, interest has been aroused in game console interfaces that can be used to control movements of characters in games. For example, devices such as joysticks or mice are generally used to control the movements of displayed game characters, but more recently there has been an introduction of interfaces which control the movements of a displayed virtual character corresponding to the physical movements of a user.

To generate such movements of a three-dimensional (3D) virtual character corresponding to motions of a user, a skeleton model with given lengths and virtual joints is defined, with the virtual joints having the same degree of freedom as human joints. Here, infrared markers or inertial sensors are attached to each joint of a human body to measure the movement angle of the respective joint. Subsequently the location (x, y, z) and angles ($\phi$, $\theta$, $\psi$) of each joint are calculated by way of forward kinematics. These calculated locations and angles can then be used to define movement of the 3D virtual character, which may be referred to as avatars, for example.

FIG. 20 illustrates such a conventional method of capturing and demonstrating motion of an individual. In operation S2000, sensor values are captured through N multiple sensors positioned at N body portions of the individual, as noted above the sensors could be inertial or infrared markers. In operation 2010, locations and rotational angles are then extracted from the sensed movement or position for each of the N body portions. Here, primarily only the positions and rotational angles of each body portion having a sensor may be determined, without estimation of positions or rotation angles, resulting in the number of required sensors being equal to the number of joints of the body being modeled. Lastly, in operation S2020, the extracted locations and rotation angles are used to generate a virtual character.

International Patent Application WO 2007/058526, the disclosure of which is incorporated herein, demonstrates an example inertial sensor that can detect position and orientation/rotational changes, e.g., by twice integrating the detected free acceleration of the inertial sensor to yield a position value. The inertial sensor can be recalibrated by adding a magnetic field sensor and using detected magnetic field information for calibrating the inertial sensor. Here, a transmitter broadcasts one or more magnetic pulses in different spatial directions. For example, the different magnetic pulses can be generated by three differently oriented coil systems, each generating a magnetic field along respective different spatial directions. The magnetic field detector is used for periodically providing different position/orientation information relative to a positioning of the transmitter that can be used to recalibrate the inertial measurement unit. Similar to the method of FIG. 20, the position and orientation changes of each sensor would be matched to each body part being modeled. Also see Inertial Sensing of Human Movement, H. J. Luinge, PhD thesis, Dec. 2002, which discusses such inertial sensors.

Thus, with numerous sensors, a sufficient amount of information can be obtained with regard to a given human skeleton model, and the human motion can thus be represented with comparatively high accuracy on a 3D virtual character through defined equations. However, to this end, a great number of sensors need to be attached to the body. In addition, with so many sensors it becomes difficult to institute corrections after an initial measurement is made. Moreover in terms of system costs, such an arrangement is typically not appropriate as an interface for home game consoles, such as those providing 3D games, since expensive equipment is required to implement the information collection and analysis. For example, in general, such systems require optical motion capture equipment such as OptoTrak (NDI) for high-accuracy motion capture. In using such optical motion capture equipment, an externally installed camera system needs to be large enough to capture all markers attached to the body, or a numerous number of cameras are required. Hence, for wider applications, it is more desirable to effectively create motion of a 3D virtual character from the measured body movement using less sensor information, if possible.

There have been studies on the representation of human movement through the use of fewer sensors. In one configuration of Hiroyuki Ukida et. al, Human Motion Capture System Using Color Markers and Silhouette, IMTC 2006, Italy, Apr. 2006, such representation requires locations and angles of movement of a body be extracted from external coordinates or markers. Consequently, there is a substantial amount of external equipment that is needed to ensure the view of the camera and to accommodate the required parallel processing of data and image information, as a similar substantial amount of information is required for generating actual motions. In another configuration of Ludovic Saint-Bauzel et. al, Real-time human posture observation from a small number of joint, IROS 2007, San Diego, Oct. 2007, a machine learning technique is implemented which only enables the distinguishing of given gestures such as a user sitting or standing. However, these example techniques are not efficient in representing general human movements. Further, such techniques are not appropriate for more user friendly application platforms such as home computers or game consoles.

Accordingly, as conventional systems require as much information as possible to represent more natural movements of a virtual character, a significant number of sensors need to be attached on a body for sampling, which results in increased costs, and requires additional computational power, while limiting correction capabilities after the initial measurements are made. Such an arrangement is accordingly not appropriate for most applications, including for generating a virtual character to be used as an interface of a home computer or game console. Conversely, a system that requires fewer components and sensors can only provide a limited amount of information, which again makes the application less desirable as only a limited number of movements can be detected, and thus only a limited number of gestures could be reflected in a displayed avatar.

SUMMARY

Accordingly, in one or more embodiments, there is provided an apparatus and a method of efficiently creating movements of a virtual character by use of a minimized number of sensors. In one or more embodiments, there is further provided an apparatus and a method of efficiently creating movements of a 3D virtual character by use of the least possible number of pieces of information.

To achieve the above and/or other aspect and advantages, one or more embodiments include a motion capture apparatus, including an estimation unit to estimate posture information, including one or more rotation angles of plural portions of a body different from a portion of the body where a measurement sensor is positioned at, based on a detected distance representation and one or more of rotation angle measurements by the measurement sensor, according to the measurement sensor being positioned at the portion of the body and detecting the distance representation between the measurement sensor and a reference position.

To achieve the above and/or other aspect and advantages, one or more embodiments include a motion capture method which maps movements of a body into a skeleton model for generating movements of a three-dimensional (3D) virtual character, the method including estimating posture information, including one or more rotation angles of plural portions of a body different from a portion of the body where a measurement sensor is positioned at, based on a detected distance representation and one or more of rotation angle measurements by the measurement sensor, according to the measurement sensor being positioned at the portion of the body and detecting the distance representation between the measurement sensor and a reference position.

The plural portions of the body may include another portion of the body having plural freedoms of motion, and the estimating of posture information for the other portion of the body may not be not based on measured posture information by the other portion of the body. In addition, the portion of the body where the measurement sensor is positioned at may have plural freedoms of motion.

Further, the distance representation between the measurement sensor and the reference position may define a side of a triangle, with two other sides of the triangle being defined by two respective distances between portions of the body, and the estimating may further include estimating the posture information by defining at least one interior angle of the triangle.

Still further, the estimating may further include defining a parallelogram, based on the distance representation between the measurement sensor and the reference position, to represent alternative positions of one of the plural portions, such that sides of the parallelogram are defined by two respective distances between portions of the body.

Here, the estimating may further include selecting one of the alternative positions of the one portion as a position of the one portion based on determined overlapping points of a first sphere having a radius of the distance representation and a second sphere having a radius of one of the two respective distances.

In addition, the estimating may further include estimating the posture information by projecting into a plane one axis for one or more portions of the body and one axis of the portion of the body where the measurement sensor is positioned at to estimate posture information of the one or more portions of the body.

Still further, reference position information may be output from a reference sensor, and the measurement sensor may detect the distance representation based on receipt of the reference position information.

Here, the reference sensor may be positioned at the reference position. The reference sensor may more particularly be positioned on the body. In addition, the reference sensor may be positioned at a reference position portion of the body different from the portion of the body where the measurement sensor is positioned at and different from the plural portions of the body different from the portion of the body where the measurement sensor is positioned at.

Still further, the estimating may include one or more rotation angles of plural portions of the body different from different portions of the body where at least four measurement sensors are positioned at, based on detected distance representations respectively from the at least four measurement sensors and one or more of rotation angle measurements of the respective measurement sensors, wherein the at least four measurement sensors include the measurement sensor positioned at the portion of the body.

The method may further include generating a 3D virtual character corresponding to the body by use of the one or more rotation angles and position coordinates of the plural portions of the body and the portion of the body where the measurement sensor is positioned at.

Further, the posture information of the body may be estimated based on an interpretation of the body, including the plural portions of the body, as an articulation model set having a link structure.

Here, a portion among from ends of the link, which may be a center of joint movements, may be defined as a rotation center and the estimating further includes estimating the posture information in consideration of a distance between the rotation center and the reference position.

Further, in the estimating of the one or more rotation angles and an estimating of position coordinates, when the rotation center of the link structure is co-located with the reference position, a rotation angle of a joint having one degree of freedom may be calculated before rotation angles of a joint having three degrees of freedom are calculated.

Still further, in the estimating of the one or more rotation angles and an estimating of position coordinates, when the rotation center of the link structure is not co-located with the reference position, candidates for a rotation angle and a rotation axis of a joint having one degree of freedom may be estimated, a movement plane set in consideration of a behavioral pattern of the body, and then rotation angles of previously unestimated joints calculated.

In addition, the one or more rotation angles and an estimating of position coordinates of the plural portions may be restricted or a movement plane determined according to situations in consideration of a human behavioral pattern in order to estimate one or more rotation angles and the position coordinates.

In addition, the body may be a human body, wherein the estimating further includes estimating posture information, including one or more rotation angles of the plural portions of the body different from rotation angle measurements of measurement sensors positioned at each of a head, wrists, and ankles portions of the body, based on detected distance representations by the measurement sensors, and one or more rotation angles for each portion of the body measured by the measurement sensors, wherein the measurement sensors respectively detect the distance representations between each measurement sensor and the reference position.

Here, at least one of the measurement sensors positioned at each of the wrists and ankles may be attached to respective portions of the body physically adjacent to the respective wrists and ankles.

The reference position may be at a center portion of the body or not on the body.

To achieve the above and/or other aspect and advantages, one or more embodiments include a motion capture apparatus, including an estimation unit which estimates posture information, including one or more rotation angles of non-extremity portions of a body based on one or more detected distance representations and rotation angle measurements measured by one or more measurement sensors, with the non-extremity portions including at least one of both an elbow and a shoulder and both a knee and a pelvis based on the one or more measurement sensors being positioned at a corresponding wrist area and/or ankle area of the body based on which non-extremity portions of the body posture information is being estimated by the estimation unit, wherein the one or more measurement sensors are positioned only at respective different extremity portions of the body and respectively detect the one or more distance representations as between each measurement sensor and a reference position.

The motion capture apparatus may further include the one or more measurement sensors to be positioned only at the different extremity portions of the body and to respectively detect the one or more distance representations.

To achieve the above and/or other aspect and advantages, one or more embodiments include a motion capture method, including estimating posture information, including one or more rotation angles of non-extremity portions of a body based on one or more detected distance representations and rotation angle measurements measured by one or more measurement sensors, with the non-extremity portions including at least one of both an elbow and a shoulder and both a knee and a pelvis based on the one or more measurement sensors being positioned at a corresponding wrist area and/or ankle area of the body based on which non-extremity portions of the body posture information is being estimated by the estimating, wherein the one or more measurement sensors are positioned only at respective different extremity portions of the body and respectively detect the one or more distance representations as between each measurement sensor and a reference position.

The motion capture method may further include detecting the one or more distance representations by the measurement sensors.

If 2D position information of a portion of the body (e.g. by means of 2D image sensor), where the measurement sensor is positioned at, is additionally available with the distance measurement, 3D position of the portion of the body can be directly calculated, and thus, the estimation process for the other portion of the body, where the measurement sensor is not positioned at, can be more simplified.

Additional aspects and/or advantages will be set forth in part in the description which follows and, in part, will be apparent from the description, or may be learned by practice of the invention.

BRIEF DESCRIPTION OF THE DRAWINGS

These and/or other aspects and advantages will become apparent and more readily appreciated from the following description of the embodiments, taken in conjunction with the accompanying drawings of which.

DETAILED DESCRIPTION OF EMBODIMENTS

Figure 1:
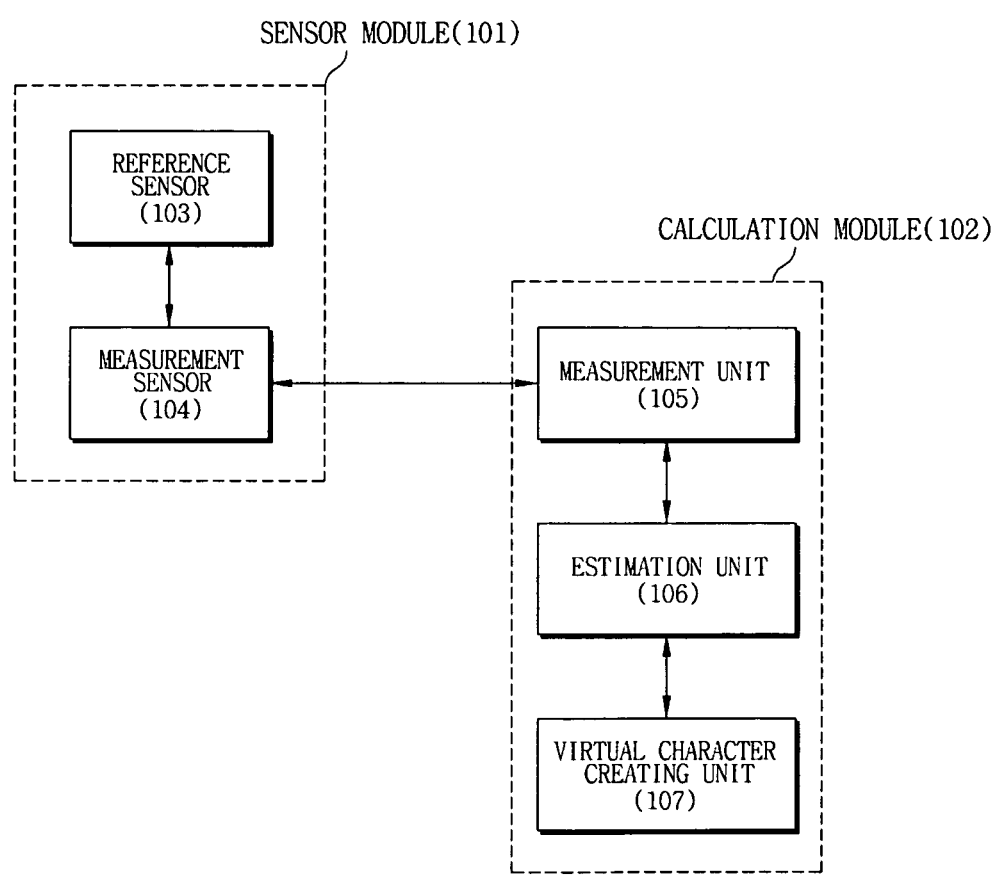
FIG. 1 illustrates a motion capture apparatus, according to one or more embodiments.

Reference will now be made in detail to embodiments, examples of which are illustrated in the accompanying drawings, wherein like reference numerals refer to like elements throughout. In this regard, embodiments of the present invention may be embodied in many different forms and should not be construed as being limited to embodiments set forth herein. Accordingly, embodiments are merely described below, by referring to the figures, to explain aspects of the present invention.

FIG. 1 illustrates a motion capture apparatus, according to one or more embodiments. Referring to FIG. 1, the motion capture apparatus may be formed of a sensor module 101 and a calculation module 102, for example. Herein, throughout the following description, the term apparatus should be considered synonymous with elements of a physical system, not limited to a single enclosure or all described elements embodied in single respective enclosures in all embodiments, but rather, depending on embodiment, is open to being embodied together or separately in differing enclosures and/or locations through differing elements. As only another example, a respective apparatus/system or method could also be controlled through one or more processing elements/devices or implemented by a distributed network, noting that additional and alternative embodiments are equally available.

The sensor module 101 may be used to detect movement information of plural respective portions of a body, and may include a reference sensor 103 and a measurement sensor 104, for example. From this detected movement information movement information for one or more joints not defined by the detected movement information may be estimated. Herein, though some embodiments may be discussed with reference to the body being that of a human, embodiments are not limited to the same; the body may be any body for which movement may be estimated, and such an estimating of movement of the body can equally be performed based on the disclosure herein. The movement information of the portion of the body sensed by the sensor module 101 can be transferred to the calculation module 102, which may create a three-dimensional (3D) virtual character corresponding to the body and/or reflect the movement of the body onto of the 3D virtual character. To this end, the calculation module 102 may include a calculation unit 105, an estimation unit 106, and a virtual character creating unit 107, for example.

Thus, measurement sensors 104 may be positioned at differing portions of the body, and can sense movement, i.e., each measurement sensor 104 can sense movement of the respective portions of the body. Furthermore, the reference sensor 103 can provide a distance defining reference position for the measurement sensor, for when the measurement sensor 104 detects the movement of the corresponding portion of the body, and may be placed at the center or at the side of the human body during the measurement, for example, noting that alternative locations are equally available. The measurement sensor 104 and reference sensor 103 may be attached to such differing portions of the body.

As only an example, when the body is a human body, measurement sensors 104 may be respectively positioned at the head, both wrists, and both ankles to sense movements of corresponding portions of the body, and the reference sensor 103 may be positioned at a certain portion of a torso (for example, a portion around the navel) or pelvis to provide a reference position for the measurement sensors 104, noting that alternative positions for the reference sensor 103 are equally available. The reference position generated by the reference sensor 103 could represent a global reference for all measurement sensors 104. Embodiments are further not limited to a single reference position.

The measurement unit 105 may accordingly measure a distance between the reference position and the measurement sensor 104 and further measure rotation angles of the measurement sensor 104, e.g., relative to the axes of the reference sensor, a preset reference axes, or the respective axes of the measurement sensor 104, for example. Alternative relationships may also be available, for example the rotation angles of the measurement sensor 104 could be relative to the axes of a joint of the body distant from a joint of the body where the measurement sensor 104 is positioned, such as a rotation center of a shoulder of an arm or pelvis for a leg. However, for brevity herein, the rotation angles of the measurement sensor or each joint of the corresponding body herein will be mostly discussed with respect to a preset axes, such as an x-axis representing left and right directions of a body facing forward, a y-axis representing forward and backward directions, and a z-axis representing gravitational directions, e.g. upward or downward directions.

In one or more embodiments, the measurement unit 105 may be integrated together with one or more of the measurement sensors 104, integrated together with the reference sensor 103, or integrated with the illustrated calculation module 102. If the measurement unit 105 is separate from a respective measurement sensor 104 then the measurement unit 105 could connect to one or more of the measurement sensors 104, via a wireless or wired connection, for example, to measure the distance between the respective measuring positions and the reference position and the rotation angles of the respective measured positions. Here, as an example, if the measurement sensor 104 is positioned at a wrist area, the measurement unit 105 may calculate the distance between the measurement sensor 104 and the reference sensor 103 and a three dimensional rotation angle of the wrist.

Here, though the reference sensor 103 and the measurement sensor 104 are illustrated and discussed below as being separate elements, embodiments of the present invention are not limited thereto. For example, a single element could have both capabilities of acting as a reference sensor, e.g., for another measurement sensor, and acting as a measurement sensor relative to another element acting as a reference sensor. Such an element with both capabilities could operate in either or both modes. A measurement sensor that acts as a reference sensor for another measurement sensor would equally not be required to act as the reference sensor for all measurement sensors, though a first measurement sensor could equally be used as the reference sensor for all of the remaining measurement sensors and only one of the remaining measurement sensors would be needed to reciprocally act as a reference sensor for the first measurement sensor, for example.

The estimation unit 106 may use values measured by the measurement unit 105, e.g., the distance between the measured body portion and the reference position and the rotation angles of the corresponding portion to estimate posture information of each body portion. For instance, if the body is a human body and the measurement sensor 104 is positioned at the wrist area, the estimation unit 106 may use a measured distance between the wrist area and the reference sensor 103 and a measured rotation angle of the wrist to estimate the relative rotation angles and position coordinates of the wrist, an elbow, and a shoulder. As noted above, conventionally such estimation would not be possible and a measurement sensor would have to be placed at each of the wrist, elbow, and shoulder positions.

In this embodiment, the body may be interpreted as being a mixture of several joints joined to one another in a link structure, several joints can equally be separately reviewed by interpreting only respective joints in a link structure, e.g., as a portion of an overall link structure. Thus, with such link structures, the estimation unit 106 may estimate posture information based on a distance between a rotation center of a joint and the reference position. In these cases, the rotation centers may be considered the end portions of the respective link structure, which can act as the axis of the joint's movement. A shoulder area for an arm movement or a pelvis area for a leg movement can be referred to as examples of such separately reviewable link structures.

Furthermore, the estimation unit 106 may further restrict the available estimated range of rotation angle for a body part in consideration of human behavioral patterns or limit available estimated movements, such as limiting movements to be one of a rectilinear movement or a curved movement, depending on circumstances in order to estimate the posture information for that body part. Such measurement information and/or estimated positional and rotation angle information may further be stored for subsequent retrieval, such as in the situation of a user jogging along an outdoor course that can later be graphically reflected through a computer generated avatar on a display. Depending on what information is stored, corresponding memory modules could be included in the measurement and/or reference sensors, for example. In a situation where a virtual representation of the body is not immediately needed, for example, a memory module included with the estimation unit 106 may store the estimation information. Herein, though separate memory modules are referenced, embodiments should not be limited to the same, and such information may be stored in various manners, including collectively in a single memory module.

The virtual character creating unit 107 may, thus, further create a corresponding 3D virtual character based on the posture information obtained by the estimation unit 106. When the body is a human body, the created 3D virtual character may graphically correspond to the human body. Here, again, the information generated by the virtual character creating unit 107 may be recorded to a memory module for subsequent display. In one or more embodiments, the memory module may be included in the virtual character creating unit 107, for example. In addition, in an embodiment, with such collection of estimated posture information and/or virtual character information one or more embodiments may include the collective displaying of plural created avatars. The collection could be through stored and/or real-time estimated posture information and/or virtual character information. Different collected information may similarly be compared and a result of that comparison displayed, e.g., with a virtual character.

Figure 2:
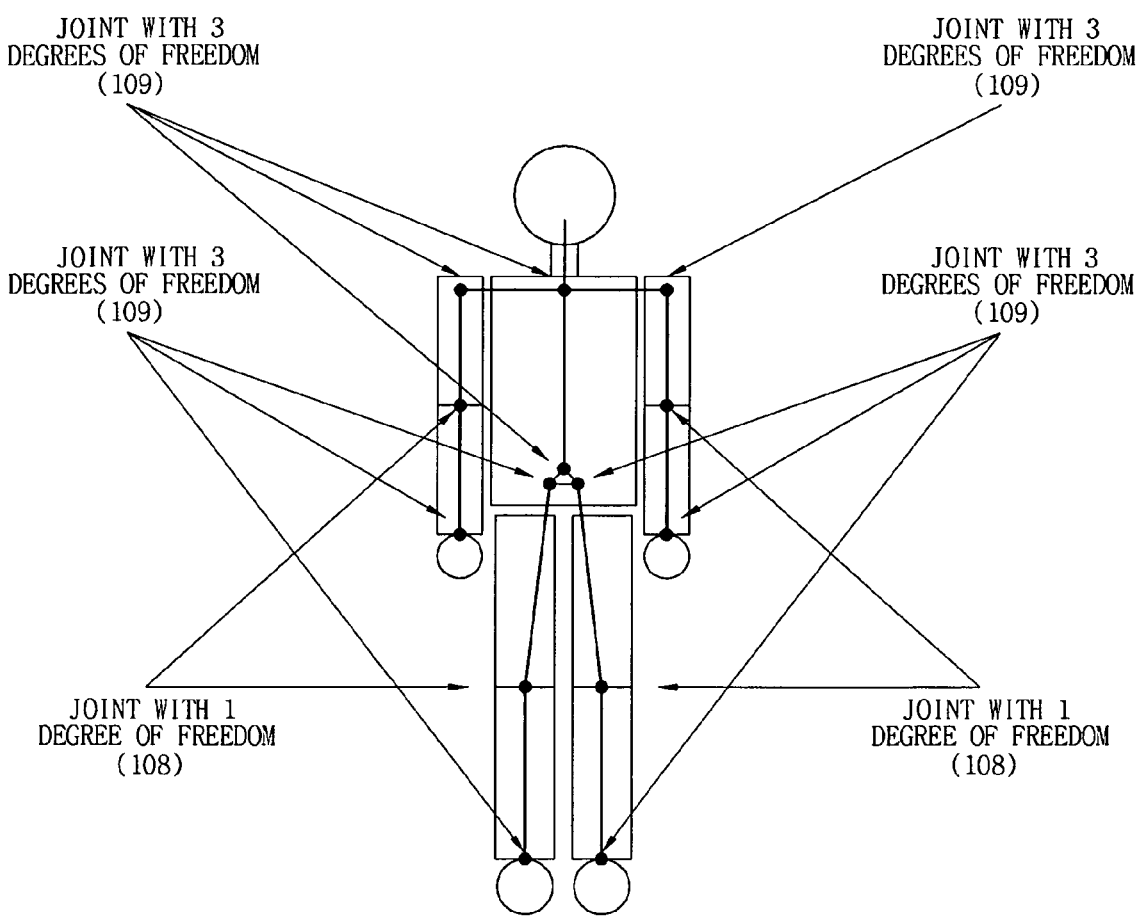
FIG. 2 illustrates a skeleton model, according to one or more embodiments.

FIG. 2 illustrates a human skeleton model, according to one or more embodiments. In FIG. 2, the human skeleton model includes four joints 108, each with one degree of freedom, and ten joints 109, each with three degrees of freedom, for a total of 34 joint degrees of freedom. As noted, the skeleton model may be interpreted as a set of joints in a link structure. The length between two adjacent joints, that is, the length of the link, may be predetermined, e.g., based on known general human body ratios, or user specific information. Referring to FIG. 2, only the elbow joints and knee joints are shown to have one degree of freedom, while the other joints are shown to have three degrees of freedom. The joints of the pelvis and a back joint may also be interpreted as sharing the same rotation axis.

Figure 3:
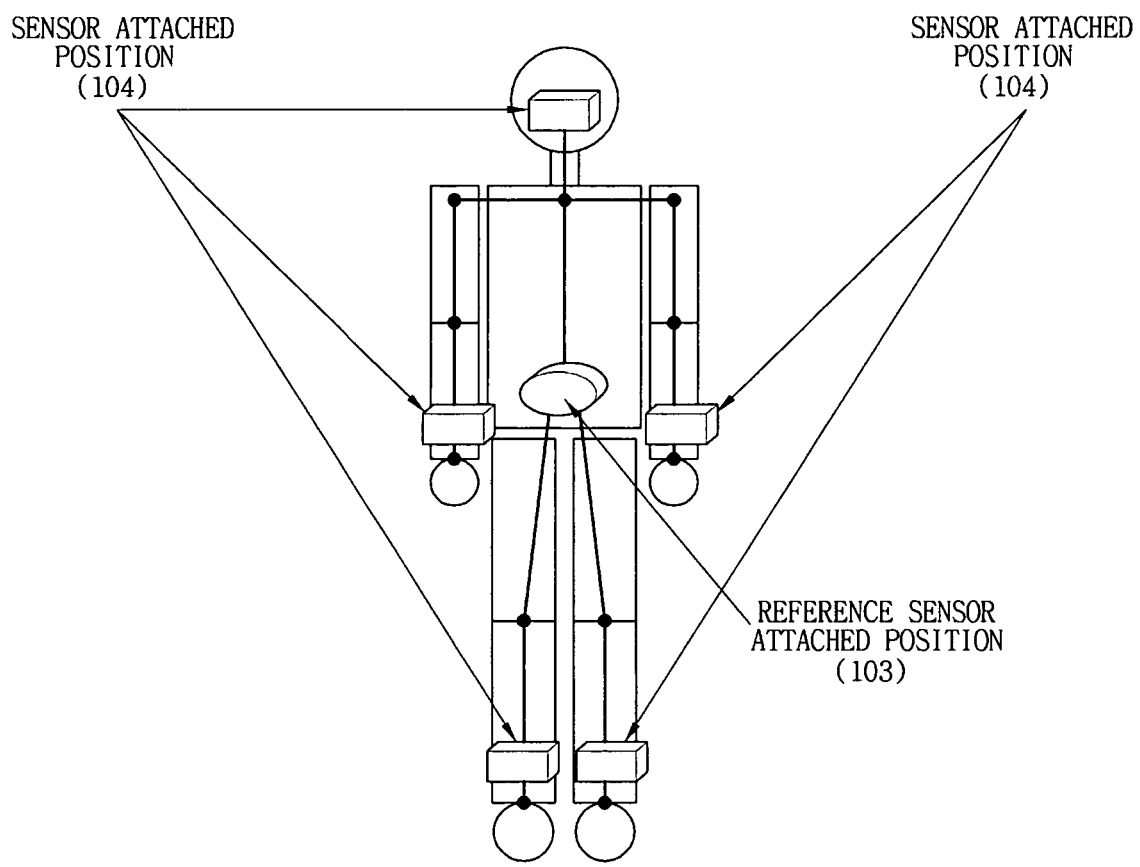
FIG. 3 illustrates portions of a body where measurement sensors and a reference sensor may be positioned, according to one or more embodiments.

FIG. 3 illustrates examples of portions of a human body where measurement sensors 104 and a reference sensor 103 may be positioned, according to one or more embodiments. Referring to FIG. 3, five measurement sensors 104 may respectively be positioned at the head, both wrists, and both ankles, and a reference sensor 103 may be positioned at the center of the torso, for example. The reference sensor 103 does not need to be positioned at the mentioned torso or pelvis, as it may be possible for the reference sensor 103 to be placed elsewhere, including at a location away from the body, i.e., not attached to the body or positioned at a portion of the body. In addition, as noted above, one or more of the measurement sensors could equally operate as a reference for other measurement sensors. When a person makes a particular motion, the measurement sensors 104 sense the movement, and the measurement unit 105 measures distances between the respective measurement sensors 104 and the reference sensor 103 and measures respective 3D rotation angles of an area where the each measurement sensor 104 is positioned.

As only an example, each of the measurement sensors 104 and the reference sensor(s) 103 may include a magnetic pulse receiving and/or transmitting device, a wireless sensor information transmitting device, an inertial sensor, and a Bluetooth device, for example. The inertial sensor may be capable of calculating 3D orientation/rotation angles of the portion of the body where the corresponding sensor is positioned. The inertial sensor may further be capable of calculating the 3D rotation angles with respect to select axes, for example, and include an accelerometer to measure an acceleration of at least one axis and an angular velocity meter to measure an angular velocity of at least one axis. In addition, since the magnetic field created by the reference sensor 103, i.e., created at the reference position, weakens at an inverse proportion to the cube of the distance from the reference sensor 103, if a magnetic pulse is transmitted by the reference sensor 103 at predetermined intervals, such as according to a predetermined clock, along one or more 3D perpendicular axes with a defined magnitude, it is possible to measure how much the magnitude of one or more of the magnetic fields for the respective x, y, and z axes has weakened upon reception by the measuring sensor 104. Accordingly, based on this determined weakening magnitude result, it is possible to measure relative distances between the respective measurement sensors 104 and the reference position.

Depending on embodiment, the types of sensors to be used are not limited to the example inertial sensors and/or magnetic sensors, and various types of sensors or sensor combinations can be used, which are available to measure relative distances between one reference position on a body or an exterior reference position and the respective sensors, and similarly various types of sensors or sensor combinations can be used for measuring the rotation angles of the respective sensors Each reference sensor 103 and measurement sensor 104 at respective positions of the body are not limited to having only one element for accomplishing the example distance measurement and/or the 3D rotation angles. For example, there may be plural example inertial sensors and/or magnetic sensors in one or more measurement sensors 104, and/or there may be plural example magnetic pulse generators/transmitters in each reference sensor 103. Regardless, for brevity of explanation, embodiments below will focus on the example of each measurement sensor 104 having such a single inertial sensor and magnetic sensor, and there being a single reference sensor 103 with the described magnetic pulse generator/transmitter.

Figure 4:
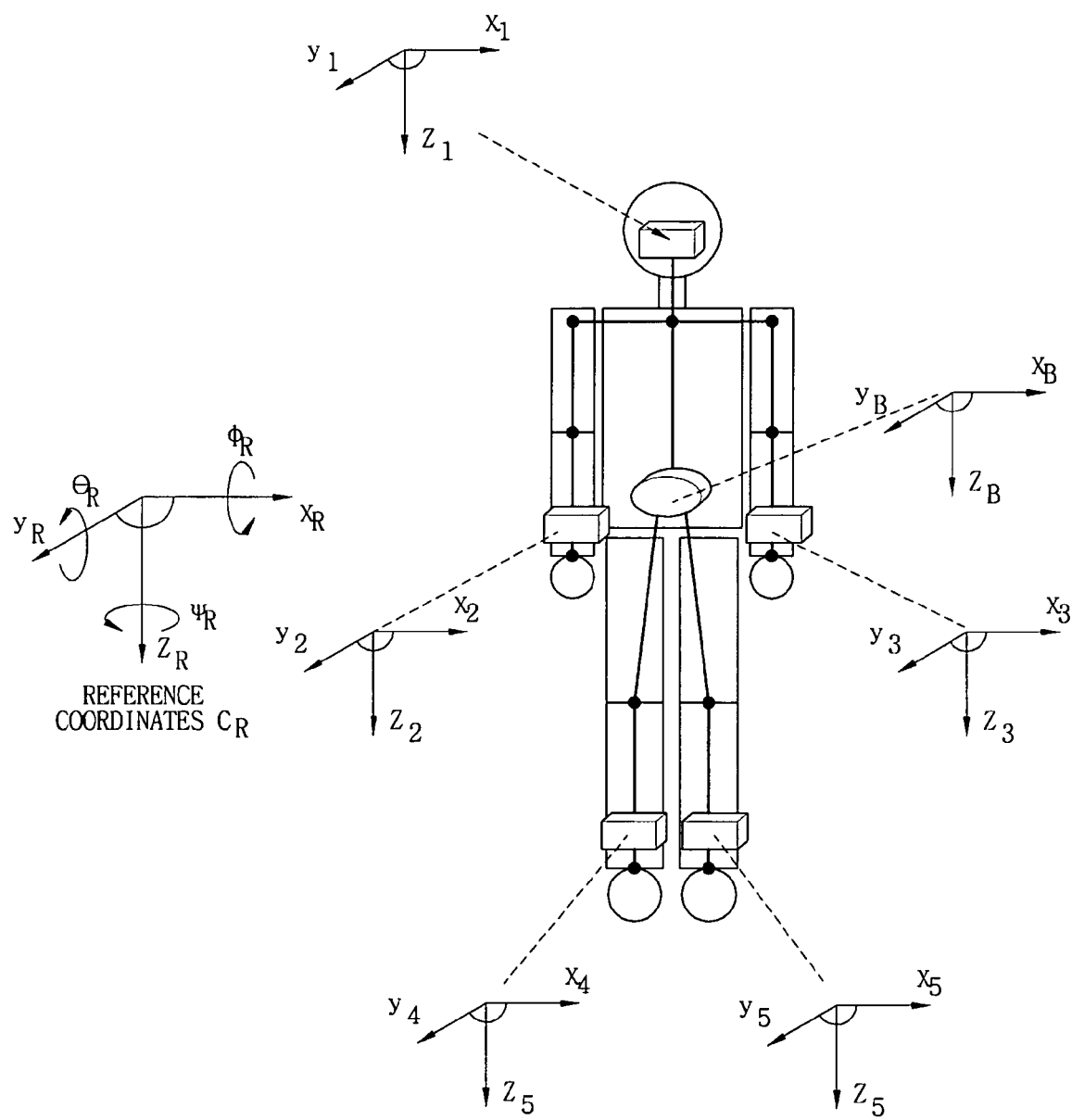
FIG. 4 illustrates reference coordinates and coordinates of measurement sensors, according to one or more embodiments.

FIG. 4 illustrates the skeleton body model of FIG. 3 with reference coordinates $C_R$ ($x_R$, $y_R$, $z_R$) with defined reference axes orientation. As noted above, and only as an example, the reference x-axis (along $x_R$) may represent horizontal left and right directions of the illustrated skeleton body, the reference y-axis (along $y_R$) may represent the forward and backward directions of the illustrated skeleton body, and the reference z-axis (along $z_R$) may represent gravitational directions, e.g. vertical upward or downward directions of the illustrated skeleton body. These reference coordinates $C_R$ may be set with an initial sampling of data, e.g., with a user standing similar to the illustrated skeleton body of FIG. 4. The potential rotation angles with respect to each axis are further illustrated in FIG. 4, i.e., the rotation angles along each of the illustrated reference axes $x_R$, $y_R$, and $z_R$. As illustrated, an angle of rotation along the reference $x_R$ axis would be $\phi$, an angle of rotation long the reference $y_R$ axis would be $\theta$, and an angle of rotation along the reference $z_R$ axis would be $\psi$.

FIG. 4 further illustrates respective sensor coordinates ($x_1$, $y_1$, $z_1$), ($x_2$, $y_2$, $z_2$), ($x_3$, $y_3$, $z_3$), ($x_4$, $y_4$, $z_4$), and ($x_5$, $y_5$, $z_5$), relative to the reference coordinates, for five positioned measurement sensors, according to one or more embodiments. As shown, and defined herein, the measurement sensors are positioned at the extremities of the skeleton body model, e.g., measurement sensors positioned at the wrists and ankles is considered a positioning at the extremities of the body, while any potential positioning corresponding to the shoulders, elbows, pelvis, and knees is not considered a positioning at an extremity. The reference sensor, providing a reference position, is illustrated as having coordinates $C_B(x_B, y_B, z_B)$.

Here, the measurement and reference sensor coordinates are illustrated along with example respective axes, with rotations for each body position being defined according to angles of rotation relative to the reference axes. Here, as shown in the skeleton body of FIG. 4, initially all axes for the measurement and reference sensors may effectively be oriented the same as the reference axis, in which case each angle of rotation for each axis would be zero. Regardless, as illustrated, the respective rotation angles for the five measurement sensors would be $(\phi_1,\theta_1,\psi_1)$, $(\phi_2,\theta_2,\psi_2)$, $(\phi_3,\theta_3,\psi_3)$, $(\phi_4,\theta_4,\psi_4)$, and $(\phi_5,\theta_5,\psi_5)$, and if the reference sensor were to rotate the corresponding rotation angle would be $(\phi_B,\theta_B,\psi_B)$ gles. Here, the initial values of coordinates and rotation angles for the reference coordinates and each of the measurement and reference sensors are not limited to the above-mentioned defined axis orientations, or corresponding relatedness, and a variety of axis orientations or coordinate systems may be employed.

Figure 5:
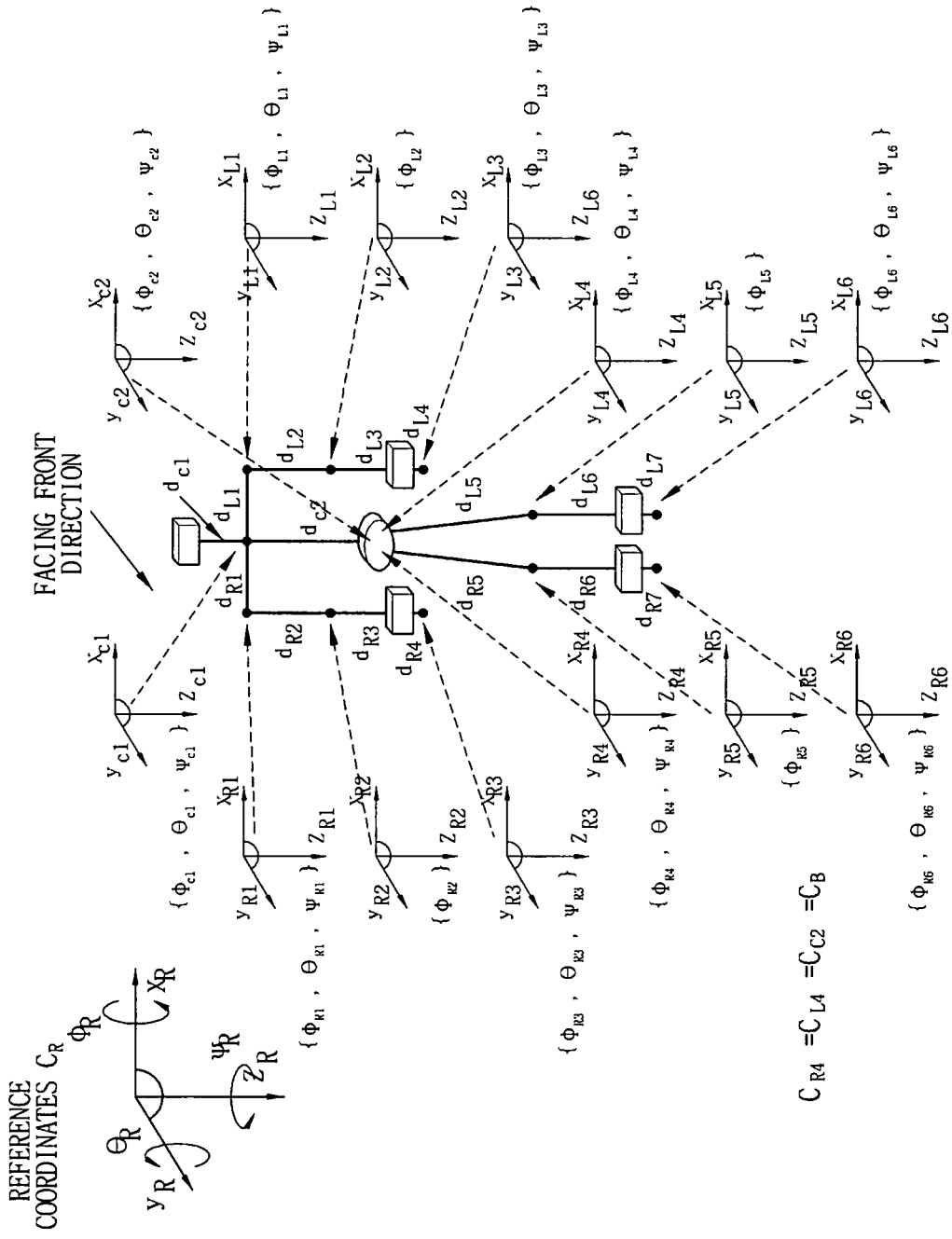
FIG. 5 illustrates example coordinates and axes with rotation of respective joints of a skeleton model, according to one or more embodiments.

FIG. 5 similarly illustrates example coordinates and rotation angles of respective joints of a skeleton model for representing positional and rotational orientation and movement. In FIG. 5, in an embodiment, it is again assumed that initially an actor is standing still, and facing the front with palms open, i.e., with palms facing the skeleton body, such that the direction which a face and feet of the actor are facing would be the respective y-axis direction, a direction which the back of the right hand is facing would be the negative direction of the respective x-axis, and a direction which the back of the left hand is facing would be the positive direction of the respective x-axis. Here, as detailed further below, the positioning of the palm of a hand can be helpful in estimating the movement of the arm as the elbow may vary freedoms of rotation based upon the orientation of the hand. Thus, each of the elbows and knees can be defined to rotate with only 1 degree of freedom, which means that each elbow and knee only moves along rotation angles $\phi$ with respect to their respective x-axes. Each joint of the skeleton model is further illustrated with example respective axes and corresponding rotation angles. As noted, at such an initial positioning of the actor, potentially the orientation of all axes for the different joints could be estimated to be aligned with the axes of the reference axes.

Accordingly, in such an embodiment, the coordinates of a joint for the head are $C_{C1}(x_{c1}, y_{c1}, z_{c1})$, the coordinates of a joint for the torso are $C_{C2}(x_{c2}, y_{c2}, z_{c2})$, the coordinates of the right shoulder are $C_{R1}(x_{R1}, y_{R1}, z_{R1})$, the coordinates of the right elbow are $C_{R2}(x_{R2}, y_{R2}, z_{R2})$, the coordinates of the right wrist are $C_{R3}(x_{R3}, y_{R3}, z_{R3})$, the coordinates of the right pelvis $C_{R4}(x_{R4}, y_{R4}, z_{R4})$, the coordinates of the right knee are $C_{R5}(x_{R5}, y_{R5}, z_{R5})$, and the coordinates of the right ankle are $C_{R6}(x_{R6}, y_{R6}, z_{R6})$. Likewise, the coordinates of the left shoulder are $C_{L1}(x_{L1}, y_{L1}, z_{L1})$, the coordinates of the left elbow are $C_{L2}(x_{L2}, y_{L2}, z_{L2})$, the coordinates of the left wrist are $C_{L3}(x_{L3}, y_{L3}, z_{L3})$, the coordinates of the left pelvis are $C_{L4}(x_{L4}, y_{L4}, Z_{L4})$, the coordinates of the left knee are $C_{L5}(x_{L5}, y_{L5}, z_{L5})$, and the coordinates of the left ankle are $C_{L6}(x_{L6}, y_{L6}, z_{L6})$.

Each of these represented joints can further be defined to have respective rotation angles relative to the respective reference axes, with corresponding $C_{C1}(\phi_{c1},\theta_{c1},\psi_{c1})$, $C_{C2}(\phi_{c2},\theta_{c2},\psi_{c2})$, $C_{R1}(\phi_{R1},\theta_{R1},\psi_{R1})$, $C_{R2}(\phi_{R2},\theta_{R2},\psi_{R2})$, $C_{R3}(\phi_{R2},\theta_{R2},\psi_{R2})$, $C_{R4}(\phi_{R4},\theta_{R3},\psi_{R4})$, $C_{R5}(\phi_{R5},\theta_{R5},\psi_{R5})$, $C_{R6}(\phi_{R6},\theta_{R6},\psi_{R6})$, $C_{L1}(\phi_{L1},\theta_{L1},\psi_{L1})$, $C_{L2}(\phi_{L2},\theta_{L2},\psi_{L2})$, $C_{L3}(\phi_{L3},\theta_{L3},\psi_{L3})$, $C_{L4}(\phi_{L4},\theta_{L4},\psi_{L4})$, $C_{L5}(\phi_{L5},\theta_{L5},\psi_{L5})$, $C_{L6}(\phi_{L6},\theta_{L6},\psi_{L6})$. Still further, the distance between the head and the center point of the shoulders $C_{C1}$ may be represented by the distance $d_{c1}$, with the distances between the right and left shoulders $C_{R1}$ and $C_{L1}$ and $C_{C1}$ respectively being $d_{R1}$ and $d_{L1}$. The distances between the shoulders $C_{R1}$ and $C_{L1}$ and the elbows $C_{R2}$ and $C_{L2}$ may respectively be $d_{R2}$ and $d_{L2}$, the distances between the elbows $C_{R2}$ and $C_{L2}$ and positions above the wrists $C_{R3}$ and $C_{L3}$, such as along a lower forearm, may respectively be $d_{R3}$ and $d_{L3}$, and the distances between the positions above the wrists $C_{R3}$ and $C_{L3}$ and the wrists $C_{R3}$ and $C_{L3}$ may be $d_{R4}$ and $d_{L4}$. Likewise, the distances between the pelvis joints $C_{R4}$ and $C_{L4}$ and the knees $C_{R5}$ and $C_{L5}$ may respectively be $d_{R5}$ and $d_{L5}$, the distances between the knees $C_{R5}$ and $C_{L5}$ and positions above the ankles $C_{R6}$ and $C_{L6}$, such as a lower shin, may respectively be $d_{R6}$ and $d_{L6}$, and the distances between the positions above the ankles $C_{R6}$ and $C_{L6}$ and the ankles $C_{R6}$ and $C_{L6}$ may be $d_{R7}$ and $d_{L7}$. Here, depending on estimation being performed, if there is an assumption that the pelvis joints are sufficiently close (co-located) to the reference position, e.g., if the reference sensor were to be positioned close to the pelvis, then the distances $d_{R5}$ and $d_{L5}$ could alternatively also be considered to be distances between the reference position and the respective knees. In such a situation, for example, the following may be assumed: $C_{R4}=C_{L4}=C_{C2}=C_B$, i.e., the positions of the right and left pelvis joints, the torso, and the reference position may be considered to be same.

Figure 6:
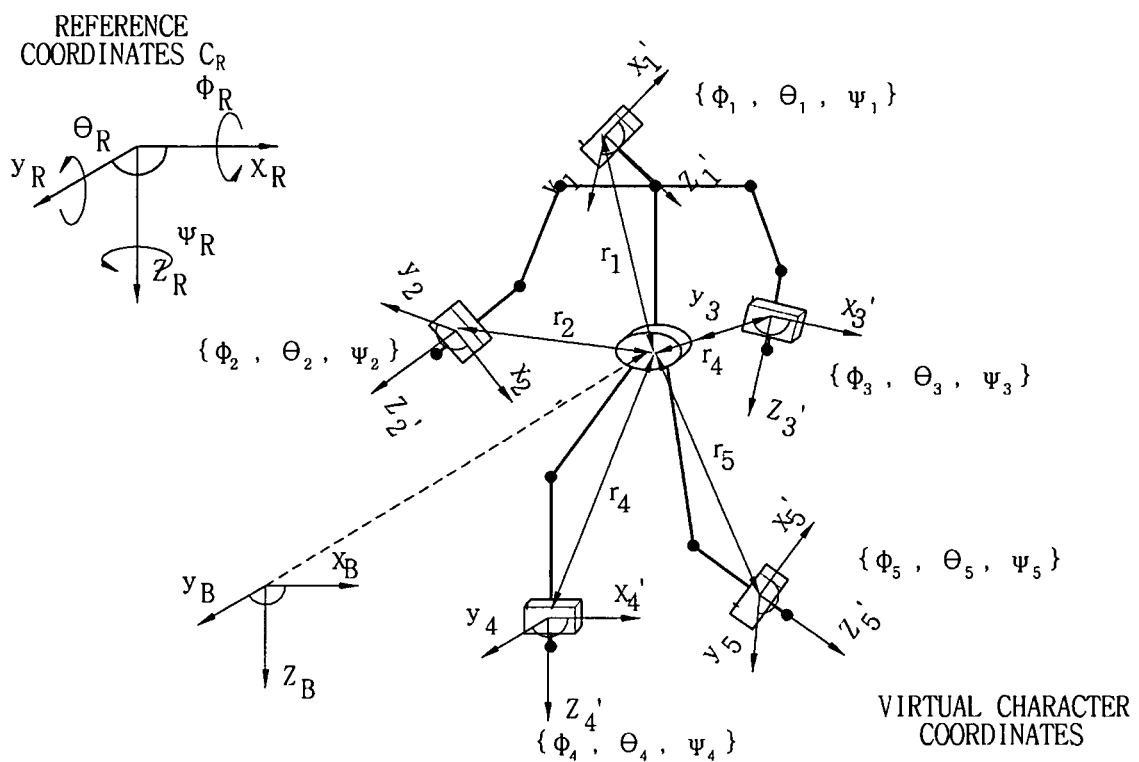
FIG. 6 illustrates sets of information representing movement information of the skeleton model, according to one or more embodiments.

FIG. 6 illustrates sets of information that can be obtained during movement of an actor with a motion capture apparatus, according to one or more embodiments, using the coordinates and rotation angles for the measurement sensors of FIG. 4. The sets of information shown in FIG. 6 may be obtained by the measurement unit 105, for example, based on respective information from the aforementioned magnetic pulse sensor and inertial sensors of each measurement sensor. Based on detection of the magnetic pulse, distances between the reference sensor, here shown positioned at the lower torso of the skeleton body, and each measurement sensor may be respectively measured to be $r_1$, $r_2$, $r_3$, $r_4$, and $r_5$. Each set of information may include the measured distance between each measurement sensor and the reference position and a 3D rotation angle of each measurement sensor, i.e., the rotation angles for each of the measurement sensors. A measured position of each measurement sensor may also be included in the respective sets of information.

The sets of information shown in FIG. 6, e.g., as obtained by the measurement unit 105, may then be transferred to the estimation unit 106, and the estimation unit 106 may further calculate values related to each joint shown in FIG. 5 based on the received sets of information. Conventionally, as noted above movements for all of the joints of the human body, such as those shown in FIG. 5, cannot be based on less than all joint position and rotation information. However, one or more embodiments efficiently create movements of a 3D virtual character even when fewer sensors are used by estimating non-measured joint position and rotation information through consideration of human behavioral patterns and appropriate assumptions based on the expected body movement involved.

Figure 7:
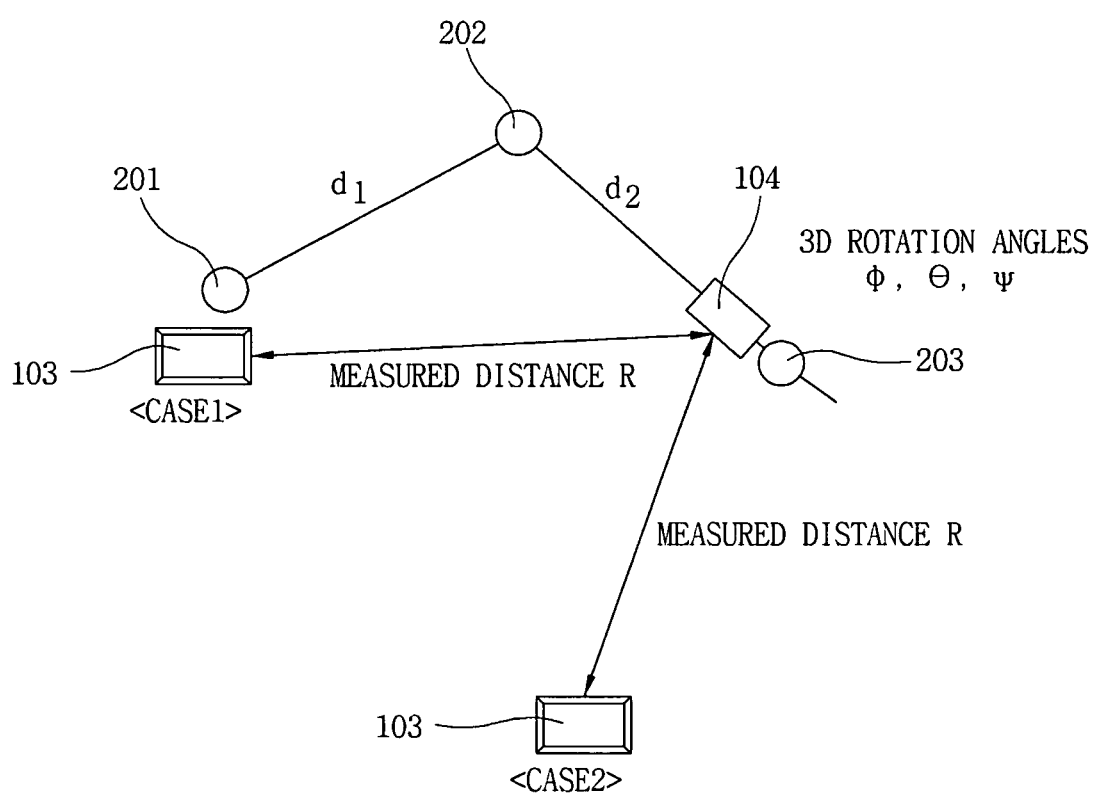
FIG. 7 illustrates a portion of a body as a link structure, according to one or more embodiments.

FIG. 7 illustrates a portion of a body as a link structure, according to one or more embodiments. An example principle of estimating posture information of a portion of the body will now be further described with reference to FIG. 7.

The link structure of FIG. 7 may represent an arm, where the rotation center 201, at the end of the link structure, corresponds to the shoulder, the first joint 202 corresponds to the elbow, and the second joint 203 corresponds to the wrist. The measurement sensor 104 is shown as being positioned just above the second joint 203, and the reference sensor is shown in two cases of being positioned near the rotation center 201 (Case1) or away from the rotation center 201 (Case2).

Under the consideration of human behavioral patterns, it is possible to estimate smooth arm movements when it is assumed that the elbow, which is the first joint 202, has only one degree of freedom, which means that the first joint 202 may only rotate in an x-axis direction. Here, in estimating movements of the wrist, i.e., joint 203, the estimation error may be insignificant if only the intact measurement values obtained by the measurement sensor 104, positioned just above the wrist, e.g., on the forearm, are used in place of estimating values for the wrist. Accordingly, here, distance d1, which corresponds to the distance between the rotation center 201 and the first joint 202, and distance d2, which corresponds to the distance between first joint 202 and the measurement sensor 104, may be preset based on known body ratios, for example.

Under such an assumption, a distance R between the reference sensor 103 and the measurement sensor 104, shown as the measured distance R for both Case1 and Case2 positioning of the reference sensor 103, and the illustrated 3D rotation angles ($\phi$, $\theta$, $\psi$) for the area where the measurement sensor 104 is positioned, may be used to calculate relative rotation angles of respective joint parts (e.g., rotation center 201, and joints 202 and 203). Based on the obtained relative rotation angles, location coordinates of the respective joint parts may be calculated by use of forward kinematic techniques.

The distance between the reference sensor 103 and the rotation center 201 may vary according to the actual positioning of the reference sensor 103, and this variance can be used for potentially simplifying subsequent joint movements estimations. For example, under the assumption that the reference sensor 103 is positioned at the torso, when the same link structure is applied to the estimation of movement of a leg, in the illustrated Case1, it may be considered that the rotation center 201 is close to the reference sensor 103, or when the link structure is applied to the estimation of the movement of an arm, in the illustrated Case2, it may be considered that the rotation center 201 corresponding to the shoulder would be far from the same positioned reference sensor 103. In this example, the closeness of the rotation center 201 in the Case1 scenario can be used of considering the rotation center of the leg and the torso to be the same effective position. The estimation unit 106 may, thus, reflect the distances between corresponding rotation centers 201 and the measurement sensor 103 on estimation or calculation of the posture information of each joint, i.e., the relative rotation angles and location coordinates of each joint. Further detailed examples will be described below.

Figure 8:
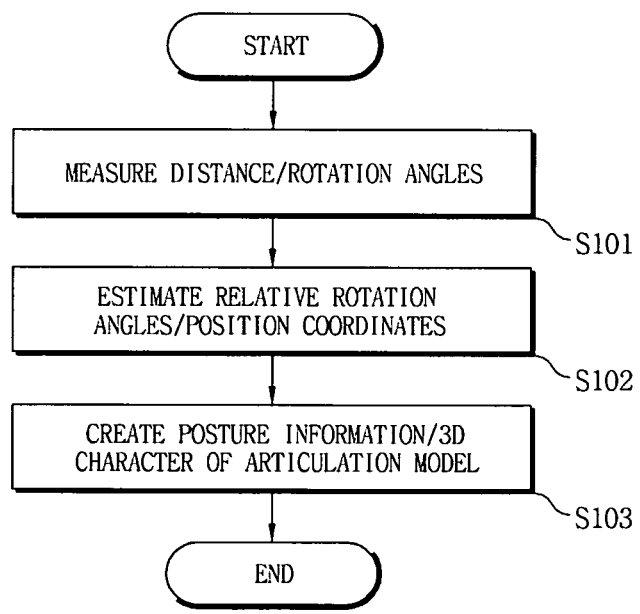
FIG. 8 illustrates a motion capture method, according to one or more embodiments.

FIG. 8 illustrates a motion capture method, according to one or more embodiments. The motion capture method may be implemented by the above-described motion capture apparatus, for example, though embodiments are not limited to the same, allowing movements of a body to be mapped into a skeleton model to generate movement estimation information and project movements onto a 3D virtual character.

Referring to FIG. 8, the motion capture method includes operations of measuring in operation S101, estimating in operation S102, and creating in operation S103, for example.

In operation S101, a distance between a measurement sensor, positioned at a body part, and a reference sensor, positioned at a reference position, and rotation angles of the measurement sensor are measured. Rotation angle(s) of the measurement sensor may accordingly be considered the rotation angle(s) of the corresponding body part where the measurement sensor is positioned. Embodiments are not limited the presently discussed limited number of measurement sensors and additional, or less, measurement sensors are equally available.

In operation S102, based on the measured distances and the rotation angles, measured in operation S101, the relative rotation angles and position coordinates of plural parts of the body may be estimated. According to one or more embodiments, the relative rotation angles and position coordinates can be estimated at any part of a body regardless of where sensors are positioned.

Related to operation S102, the body can be represented by a skeleton model having one or more link structures. In operation S102, based on characteristics of each link structure, and distances between measurement positions, reflected on the link structures, and a reference position, the relative rotation angles and the position coordinates can be obtained for all parts of the body.

Such an operation will now be described in further detail with reference to FIG. 9.

Figure 9:
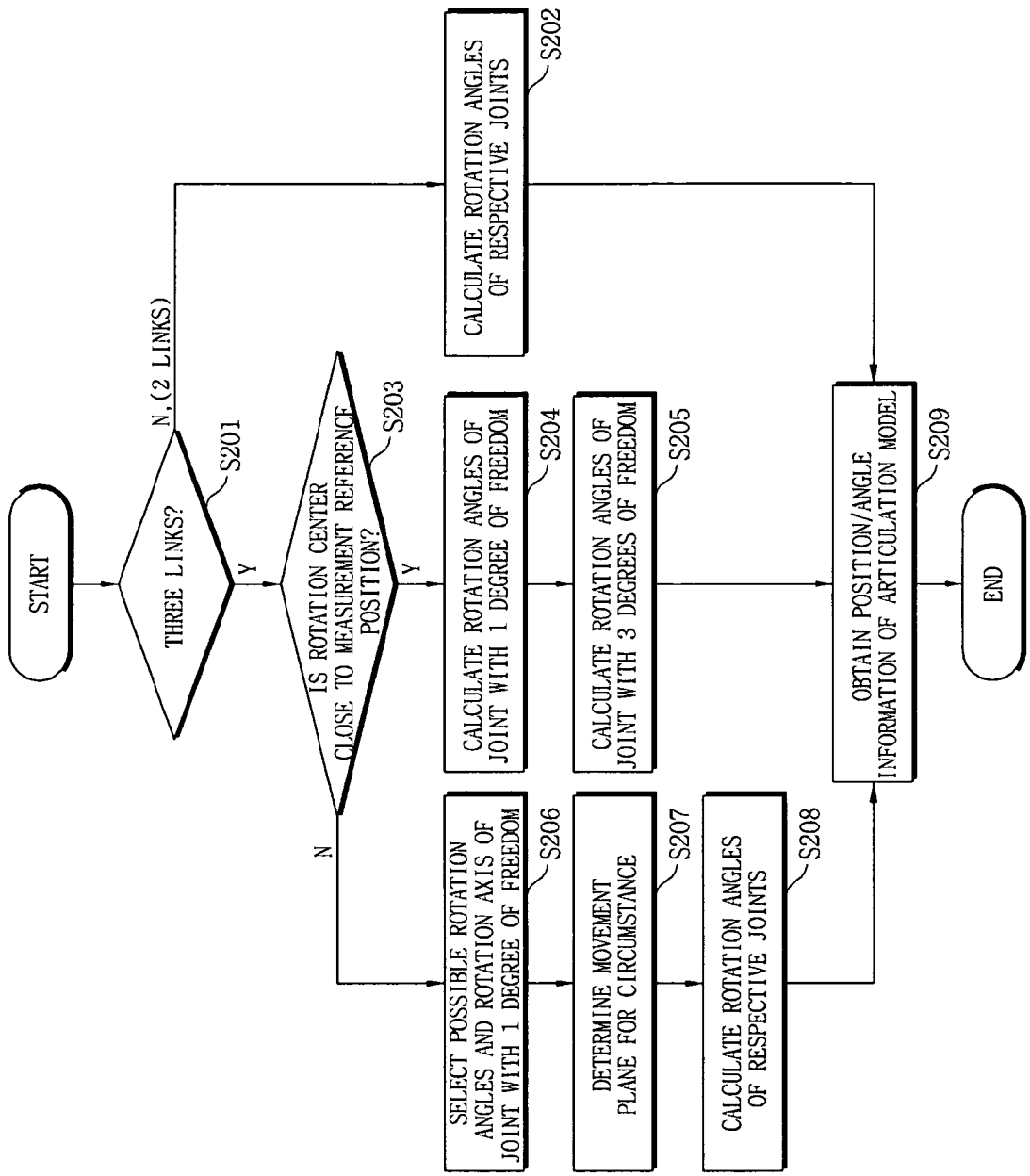
FIG. 9 illustrates procedures of estimating posture information, according to one or more embodiments.

FIG. 9 illustrates a method for calculating posture information of each joint, according to one or more embodiments.

First, characteristics of a link structure at a corresponding body portion may be examined, in operation S201. For example, a portion between a head and a torso can be regarded as a 2-link structure, and an arm composed of a shoulder, an elbow, and a wrist can be regarded as a 3-link structure. In operation S201, if the corresponding portion is not the 3-link structure (e.g., the 2-link structure portion between the head and torso), a rotation angle of a corresponding joint (e.g., a neck joint) having the one degree of freedom may be calculated, in operation S202. The positions and rotation angles of the remaining body portions of this 2-link structure (e.g., body portions between the torso and head) of the skeleton model may then be calculated, in operation S209).

In addition, in operation S201, when a corresponding portion of the body is in a three-link structure (for example, an arm composed of a shoulder, an elbow, and a wrist or a leg composed of a pelvis, a knee, and an ankle), it may be estimated whether the rotation center, e.g., the shoulder or pelvis of respective three-link structures, is close to a reference position, in operation S203. For example, when the reference position is placed at a center (for example, the navel) of a torso or pelvis, it may be estimated that the leg's rotation center (i.e., the pelvis) is close to the reference position and the arm's rotation center (i.e., the shoulder) is far from the reference position.

In such an embodiment, when it is estimated that the rotation center is near the reference position, the rotation angle of a corresponding joint (e.g., a knee) with one degree of freedom may be calculated, in operation S204, and rotation angles of the remaining joints, (e.g., the pelvis and ankles) with three degrees of freedom may thereafter be calculated, in operation S205. Subsequently, based on the rotation angles of respective joints, the corresponding positions and angles of the skeleton model may be estimated, in operation S209.

In such an embodiment, when it is estimated that the rotation center is not close to the reference position, candidates for a rotation angle and a rotation axis of a corresponding joint (e.g., an elbow) with one degree of freedom may be estimated, in operation S206, representative movement planes may then be set according to a predetermined or determined movement assumption(s), in operation S207, and the rotation angles of each corresponding joint (e.g., a wrist, an elbow, and a shoulder) may be calculated, in operation S208. Then, in a similar manner as described above, the positions/angles of the skeleton model may be obtained based on the rotation angles of each joint, in operation S209.

During the calculation of the rotation angles of respective joints, estimation for the joints may be based on the aforementioned movement assumption, which may include a restriction of movement or rotation of a joint to a particular range in consideration of human behavioral patterns, and/or a setting of an appropriate range of movement for the joint in consideration of actions for the estimated body, such as the estimated body being a body writing on a desk, swinging a golf club, walking, etc., for example. Additional and/or alternative restrictions on movement or rotation based on behavioral patterns or actions for the estimated body are equally available. In addition, the estimation of the positions and rotation angles may be considered a hierarchic method, as an initial estimation of positions and rotation angles for non-sampled joint positions can be used for the thereafter estimating the positions and rotation angles for remaining non-sampled joint positions.

Referring to FIG. 8 again, through operation of estimation in operation S102, relative rotation angles and position coordinates of each portion of the skeleton model may be obtained, these pieces of obtained information may further be mapped onto the skeleton model and a 3D virtual character generated, in operation S103. For example, operation S103 may enable a virtual character to be visualized on a screen or display by use of obtained information relating to each joint and a 3D graphic engine. For instance, visualization may be implemented by employing the scene graphic concept of the graphic library Open Inventor (by silicon Graphics, Inc). The skeleton model of a human may be configured as a data tree containing information of rotation angles and the lengths of links between a head or waist axis to parts near the axis. Such the skeleton model can be easily implemented in a graphic library. Moreover, the skeleton model may be implemented by use of the sub-graphic library, OpenGL. However, in the one or more embodiments, such a visualization method is not limited to a specific graphic library.

In an embodiment, the generated virtual character may be applied to a graphic game as a game character. Moreover, texture mapping may be performed on a given skeleton model, and thereby a generated virtual character can look more human, or can be represented even to be of a different character.

Furthermore, to smooth or further refine estimated movements of the virtual character, an interpolation algorithm may be added to connect movements. For example, such an interpolation algorithm may be desirable when an application platform generating the skeleton model has limited calculation capability resulting in undesirable, inadequate, or inconsistent sampling frequencies, for example.

Hereinafter, it will now be described in further detail how to obtain posture information of several portions of a body. The coordinates system in FIGS. 4 to 6 will be used for the coordinates of each portion of the body, and it may be assumed that a reference position is the center (for example, a spot around the navel) of the body.

Figure 10:
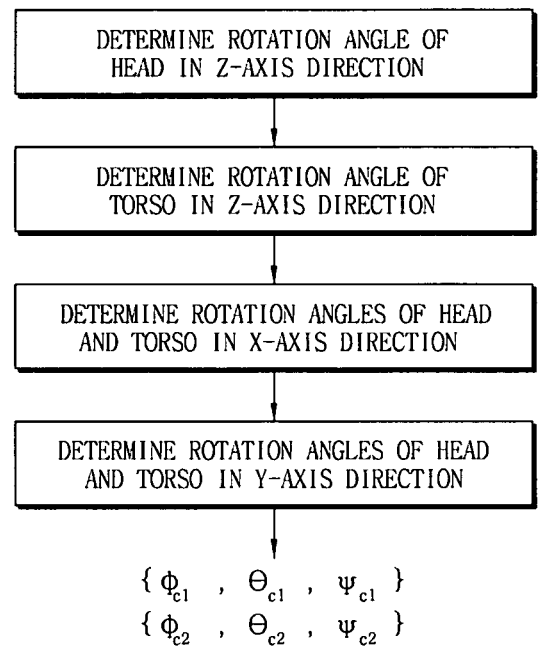
FIG. 10 illustrates procedures of estimating rotation angles of a head and torso, according to one or more embodiments.

FIG. 10 illustrates procedures for estimating rotation angles of a head and torso, e.g., the aforementioned 2-link structure, according to one or more embodiments. The rotation value in a respective z-axis direction obtained by a measurement sensor positioned at the head, i.e., $\psi_1$ shown in FIG. 4, can be used as the z-axis direction rotation angle of the head, i.e., $\psi_{C1}$ shown in FIG. 5. That is, an assumption may be made that $\psi_{C1} = \psi_1$.

Next, a facing direction of a body may be estimated based on given information. Mostly, in an embodiment, the movements of arms, legs, and the head may be assumed to convey an intended movement direction, and the direction of the torso may be estimated to show natural movements adaptively to the circumstances.

To this end, a rotation angle $\psi_{C2}$ for the torso, as shown in FIG. 5, which is a movement with respect to a z-axis, may be estimated.

Figure 11:
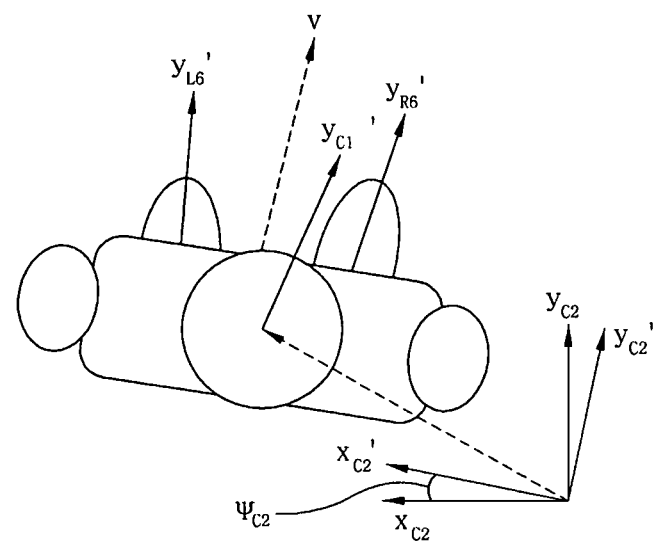
FIG. 11 illustrates a body viewed from the top of the head to explain procedures of estimating a rotation angle of the torso, according to one or more embodiments.

Accordingly, FIG. 11 illustrates a body viewed from the top of the head to explain procedures of estimating rotation angle 4)C2 of the torso, according to one or more embodiments. The facing directions of the head and the left and right ankles correspond to the illustrated orientation directions of the respective axes $y_{c1}'$, $y_{R6}'$, and $y_{L6}'$. As noted above, the rotation angle with respect to a horizontal surface may be $\psi$, i.e., a rotation angle with respect to the z-axis. This rotation with respect to the z-axis could be more easily understood as a turning left or right of a body about a fixed point.

It may first be assumed that an example human cannot turn his/her neck more than 90 degrees either left or right based on the orientation of the torso, for example. Similarly, it may further be assumed that the example human cannot turn his/her ankle more than 90 degrees either left or right based on the orientation of the leg. According to an embodiment, when analyzing active movements such as golf or martial arts, besides usual movements like walking, it may be sensible to assume that the average of vectors of facing directions of respective feet and a vector of sighting direction of eyes is regarded as a facing direction of the torso. From this concept, the rotation angle $\psi_{C2}$ of the torso may be estimated according to the below Equation 1, for example.

$$\psi_{C2} = (k_1 \psi_1 + k_2 \psi_4 + k_3 \psi_5)/(k_1 + k_2 + k_3) \quad \text{Equation 1:}$$

Here, each variable k denotes a particular weight, and $\psi_4$ and $\psi_5$ are rotation angles from measurement sensors positioned at the ankles. Since a value of the rotation angle $\psi_{C1}$ at the head may be equal to the rotation value $\psi_1$ obtained from the measurement sensor at the head position, it is thus possible to estimate the rotation angle of the torso through Equation 1, noting that embodiments are not limited to the same.

Figure 12:
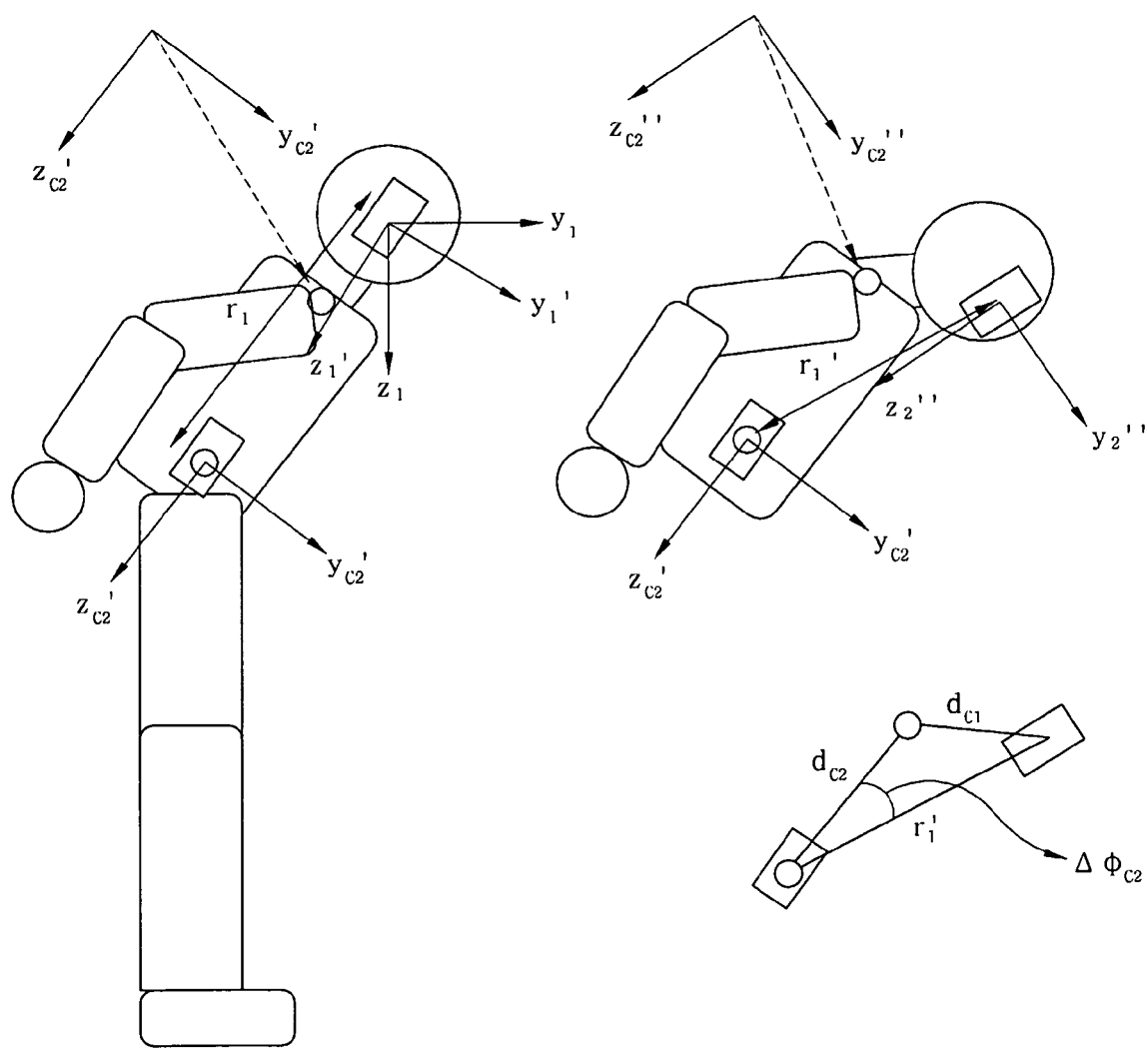
FIG. 12 illustrates a side of the body for explaining procedures of estimating the a rotation angle of the torso when the upper torso is bent, according to one or more embodiments.

Values of movements, such as for a bending of the torso forward, with the head and torso rotating with respect to an x-axis axis, for example, may be obtained as shown in FIG. 12, for example.

FIG. 12 illustrates a side view of the body for explaining example procedures of estimating the rotation angle $\phi_{c2}$ of the torso, as shown in FIG. 5, according to one or more embodiments. When only the torso is bent without bending the head, it may be considered that the rotation angle $\phi_{c1}$ of the head, as shown in FIG. 5, with respect to the x-axis is identical to the rotation angle $\phi_1$ of the measurement sensor positioned at the head, as shown in FIG. 4. However, when the neck is also bent, represented by rotation about the respective x-axis at the center point between the shoulders shown in FIG. 5, a triangle can be formed with vertices of the torso, the neck, and the head. Since the each length between joints is predetermined and the length between the torso and the head is measurable, three sides of this triangle can be obtained. Therefore, since the values of the three sides are given, three interior angles can be also calculated, and thus $\Delta\phi_{C2}$ can be obtained. Here, since $\phi_1$ is typically either equal or larger than $\phi_{C2}$ with respect to the x-axis, $\Delta\phi_{C2}$ represents the difference in rotation between $\phi_{C2}$ and $\phi_1$, i.e., $\Delta\phi_{C2} = \phi_1 - \phi_{C2}$. Therefore, rotation angle $\phi_{C2}$ among the rotation angles of the torso can be obtained by $\phi_1 - \Delta\phi_{C2}$. In the above-described embodiment, it can be determined whether or not the head is bent by comparing the distance between the torso and the head with the sum of each joint length. For example, when the head is not bent, $r_1' = d_{c1} + d_{c2}$, as the head would be directly in-line with the torso and $\Delta\phi_{C2} = $ zero, and alternatively, when the head is bent, $r_1' > d_{c1} + d_{c2}$.

Example procedures for estimating the rotation angle $\theta_{c2}$ of the torso, as shown in FIG. 5, with respect to a respective y-axis and the rotation angle $\theta_{c1}$ of the head, as also shown in FIG. 5, with respect to the respective y-axis may be considered to be similar to the above procedures for estimating $\phi_{c2}$ of the torso with respect to the respective x-axis. This rotation with respect to the y-axis could be more easily understood as a leaning left or right of a body part about a fixed point.

Figure 13:
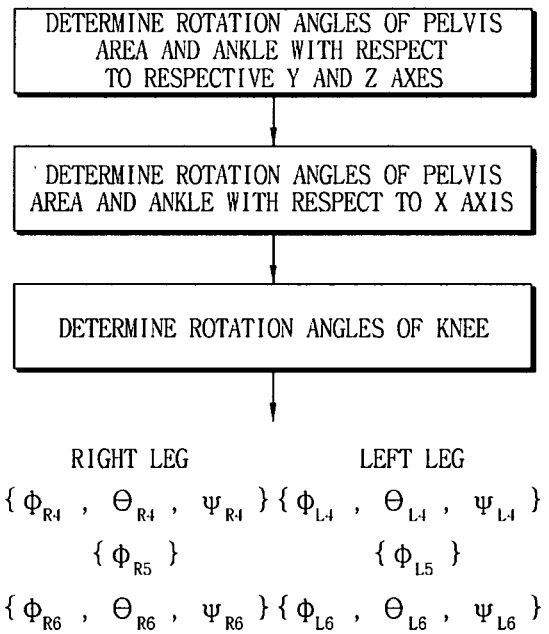
FIG. 13 illustrates procedures of estimating rotation angles of each leg, according to one or more embodiments.
Figure 14:
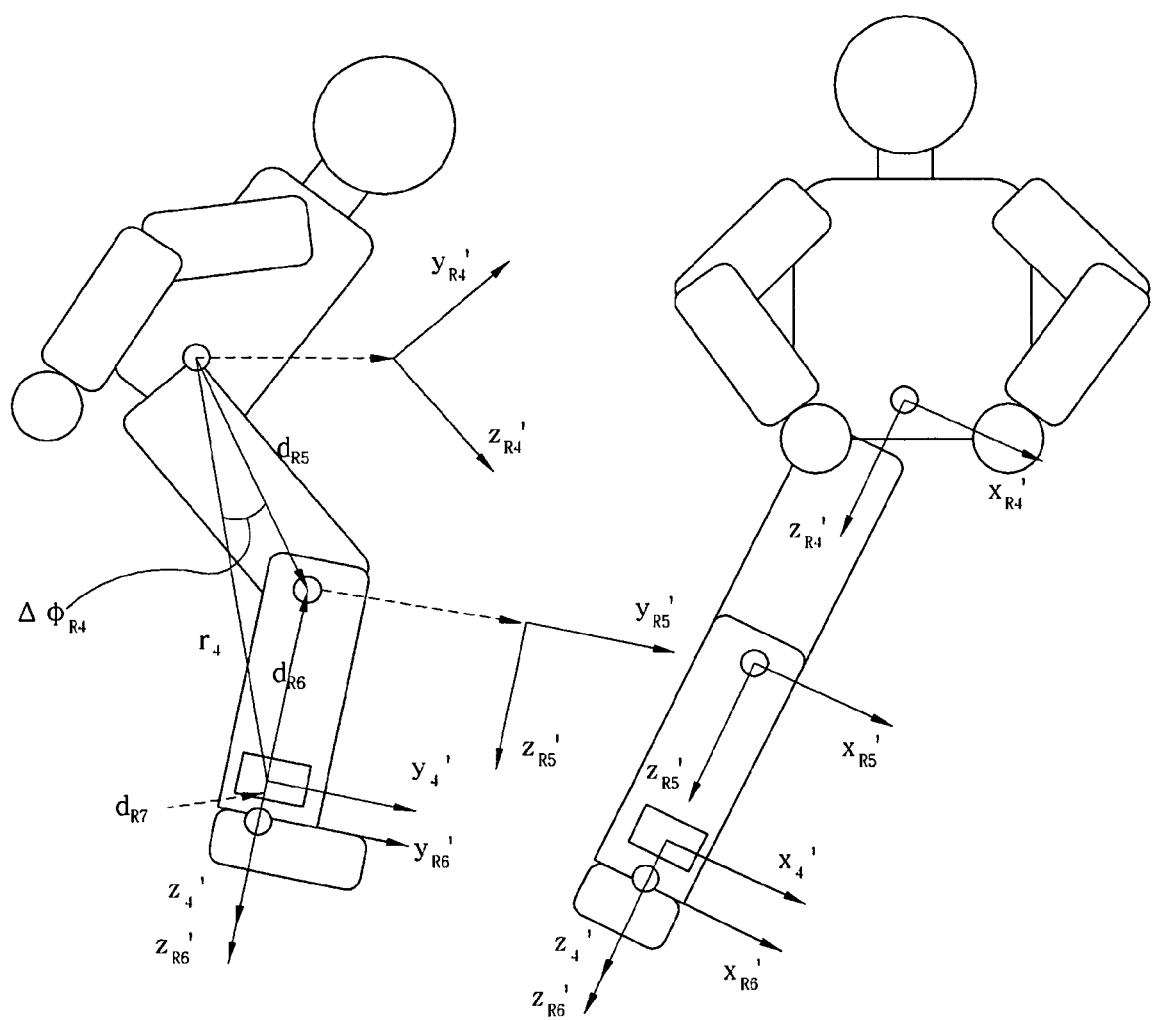
FIG. 14 illustrates a leg of a body for explaining procedures of estimating movements of a leg, according to one or more embodiments.

FIG. 13 illustrates example procedures for estimating the rotation angles for both legs, according to one or more embodiments. For facilitation of explanation, description will now be provided based on the right leg, as shown in FIG. 14. As noted above, the leg can be considered to have seven degrees of freedom, including three degrees of freedom for the pelvis joints, three degrees of freedom for each ankle, and one degree of freedom for each knee. In this case, in an embodiment, there may be an assumption that there are no significant differences in representing the general form of the movements even when the coordinates of the right ankle, as shown in FIG. 5, of three degrees of freedom change in conjunction with the shin, where the corresponding measurement sensor may actually be positioned. Hence, in an embodiment, it may be assumed that the shin and the ankles are bonded together. Still further, as noted above, there may be an assumption that the pelvis, as a rotation center of the three-link structure, and the reference position are close, such as when the reference sensor is positioned at the torso or pelvis. Here, there may be an assumption that there is no distance between the pelvis and the reference position or torso. Thus, a measured distance between the measurement sensor and the reference position can be considered to be equally the distance between the measurement sensor and the pelvis.

Since the knee joint can be assumed to have only one degree of freedom along rotation angle $\phi_{R5}$ with respect to an the $x_{R5}'$ axis, i.e., with only changes in the rotation angle $\phi_{R5}$ due to movements of the knee joint, and the z-axes are in the same plane, the rotation angles $\theta_{R4}$ and $\psi_{R4}$ for a corresponding pelvis joint and $\theta_{R6}$ and $\psi_{R6}$ for the ankle joint, both shown in FIG. 5, will have the same values as the rotation angles $\theta_4$ and $\psi_r$ for the measurement sensor positioned at the right ankle. That is, $\theta_{R4}=\theta_{R6}=\theta_4$, and $\psi_{R4}=\psi_{R6}=\psi_4$. In addition, since the ankle and the shin are bonded together, the rotation angle $\phi_{R6}$ for the ankle can be considered to be equal to the rotation angle $\phi_4$ for the measurement sensor, which may more actually be positioned at the shin of the user, for example. Moreover, a triangle can similarly be formed by the distance $r_4$ between the measurement sensor positioned at the shin and the reference position, i.e., measured by the measurement sensor, the length $d_{R5}$ between the pelvis (assumed to be sufficiently collocated with the reference position) and the knee, and the length $d_{R6}$ of the lower leg, with $d_{R5}$ and $d_{R6}$ being predetermined. From this triangle it is possible to obtain three interior angles, including $\Delta\phi_{R4}$. Thus, the representative triangle can rotate by $\phi_{R6}$ with respect to the gravitational direction, and the rotation angle $\phi_{R5}$ for the knee can be calculated from the rotation angle $\phi_{R6}$ of the ankle.

These example procedures have been described as being performed under the condition where the reference position is the navel or the pelvis, that is, where the rotation axis of the leg is close to the reference position. However, if the reference position is not close to the rotation axis of the leg, the respective procedures of estimating movements of the leg may be performed by a method similar to that of estimating movements of an arm, which will be described in more detail below.

Although the above discussion is with regard to a right leg, the left leg may be assumed to be symmetrical to the right leg and similar procedures may be applied.

Figure 15:
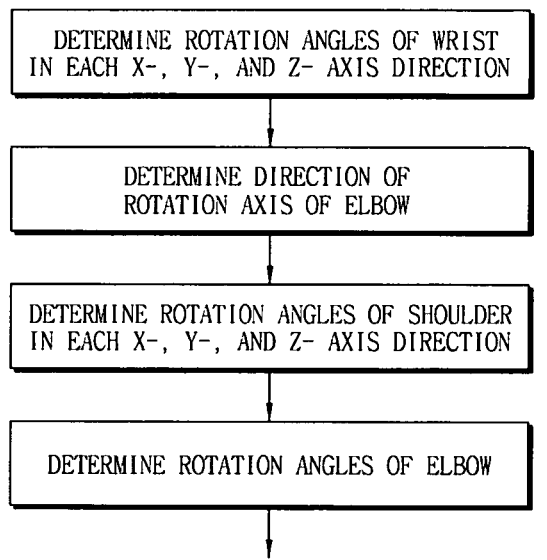
FIG. 15 illustrates procedures of estimating rotation angles of each arm, according to one or more embodiments.

FIG. 15 illustrates procedures of estimating rotation angles of each arm, according to one or more embodiments. For facilitation of explanation, the procedures will be described based on the right arm. Similar the above discussion regarding the positional relationship between the shin and the ankle, as long as fine movements of the wrist are not considered, it is typically not problematic to realize natural arm movements even when it is assumed that the axis from the lower arm to the wrist and the axis of the wrist are fixed, e.g., in the situation where the measurement sensors are positioned at the respective lower arms near the wrists. Hence, an important factor for estimating the arm's movement may be a three-degree of freedom coordinates $C_{R1}$ of the shoulder and a rotation angle $\phi_{R2}$ of the elbow, which can be calculated from the measurement sensor information.

Figure 16:
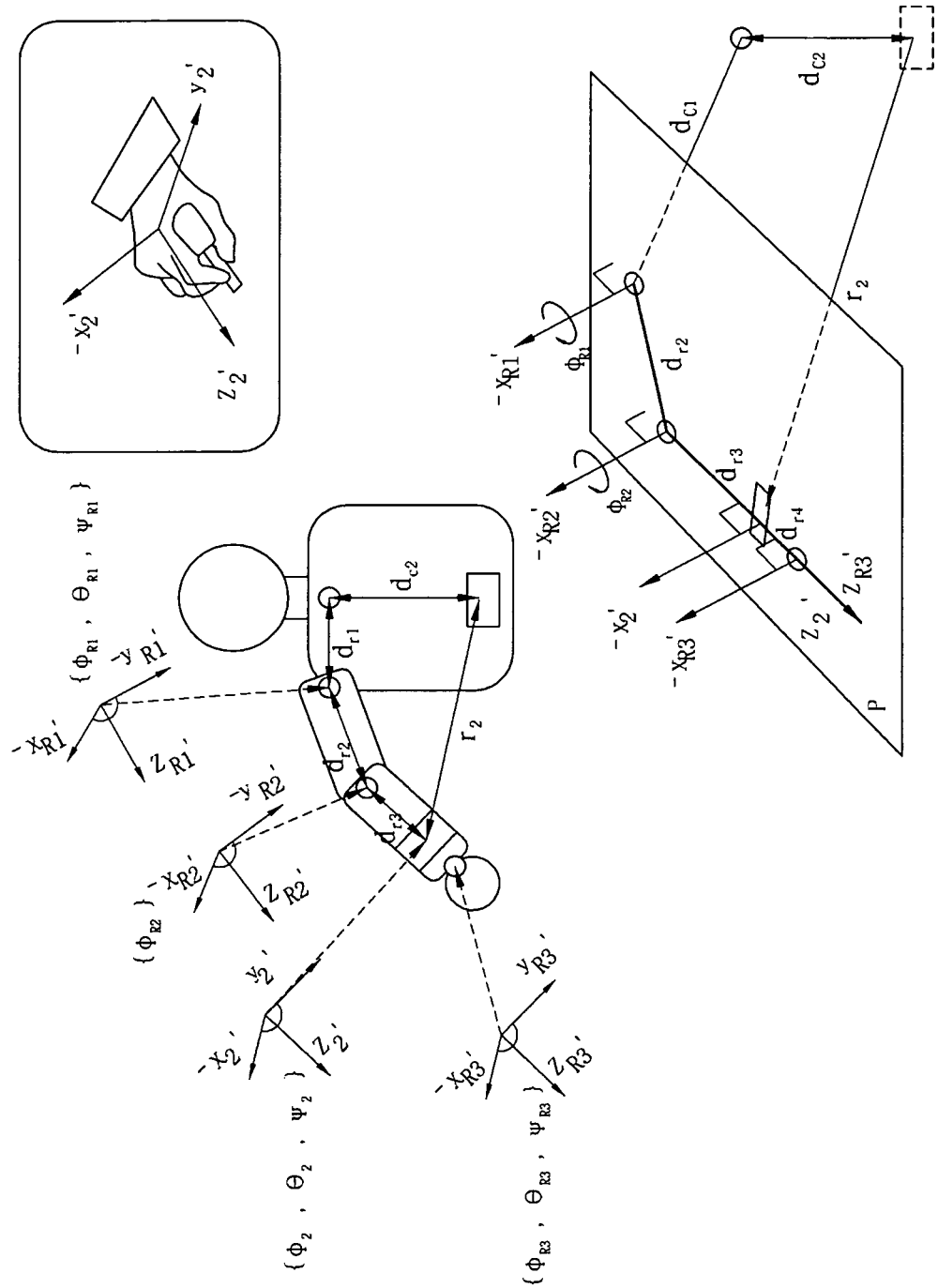
FIGS. 16-19 illustrate an arm of a body for explaining procedures of movements of each arm, according to one or more embodiments.

Referring to FIG. 16, it can be seen that a movement along rotation angle $\phi_{R3}$ for the wrist, which is the arm's movement with respect to an $x_{R3}$-axis, is restricted the most. For this reason, to ensure the maximum range for the natural arm movement, an axis $x_{R2}$ of the elbow for the arm's rotation degree of freedom may be considered to be parallel to the axis $x_{R3}$ of the wrist, and three consecutive joints of the respective shoulder, elbow, and wrist may be in the represented plane P.

Figure 17:
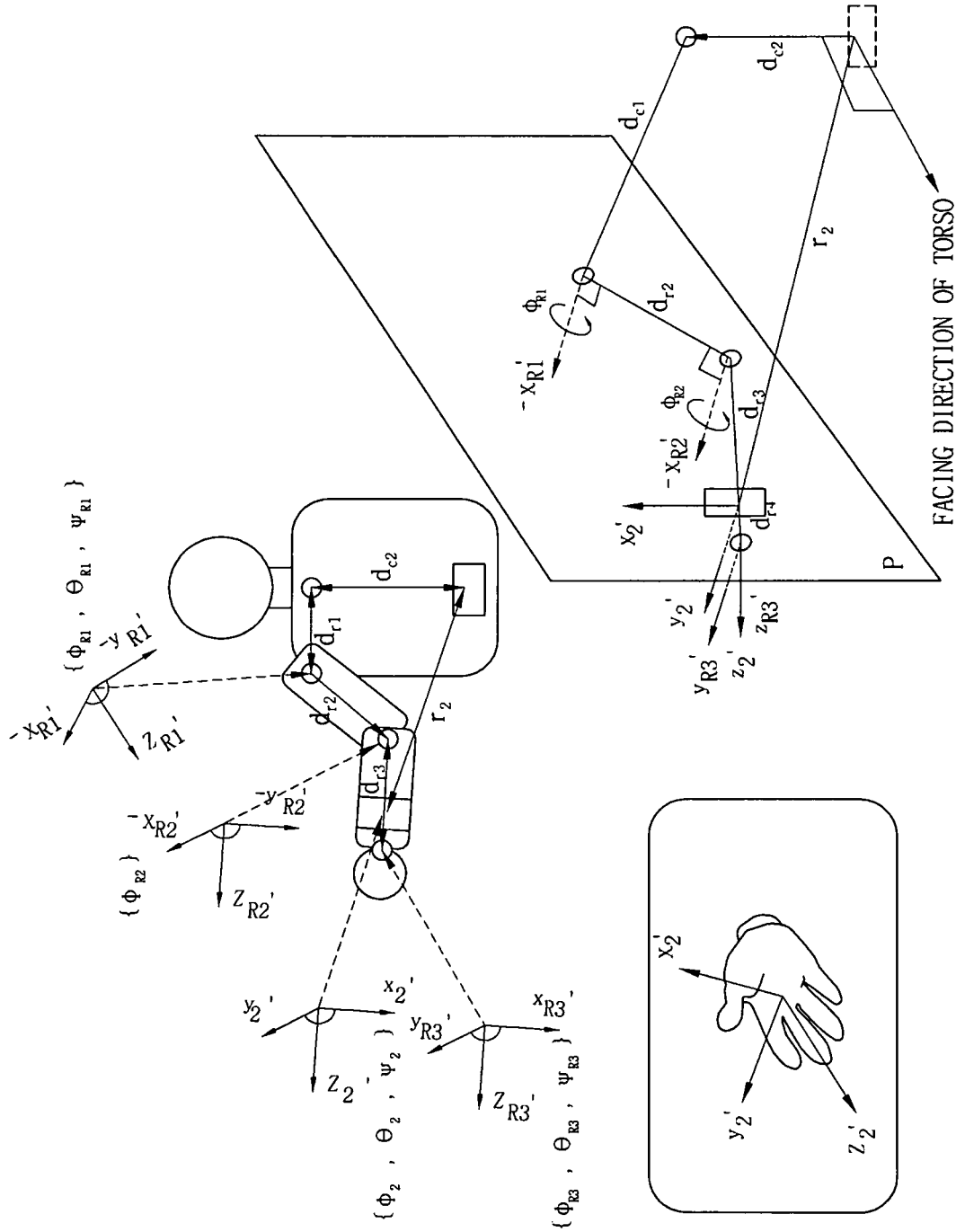

On the contrary, a wrist movement $\psi_{R3}$ with respect to a $z_{R3}$ axis may be restricted within a range from $+\pi$ to $-\pi/2$. In this case, it may be considered that $\psi_{R3}$ is greater than 0 when the arm is lowered while the back of the hand is facing the body, and $\psi_{R3}$ is smaller than 0 when the arm is still lowered while the back of the hand is facing away from the body. In the case of where $\psi_{R3}$ is greater than 0, if the axis $x_{R2}$ of the elbow's rotation degree of freedom is disposed to be parallel to the axis $x_{R3}$ as described above, natural movements can be realized. However, in other cases when $\psi_{R3}$ is smaller than 0 (for example, when the palm faces up), more natural movements may be realized by disposing $x_{R2}$ to be parallel to an axis $y_{R3}$ as shown in FIG. 17.

Figure 18:
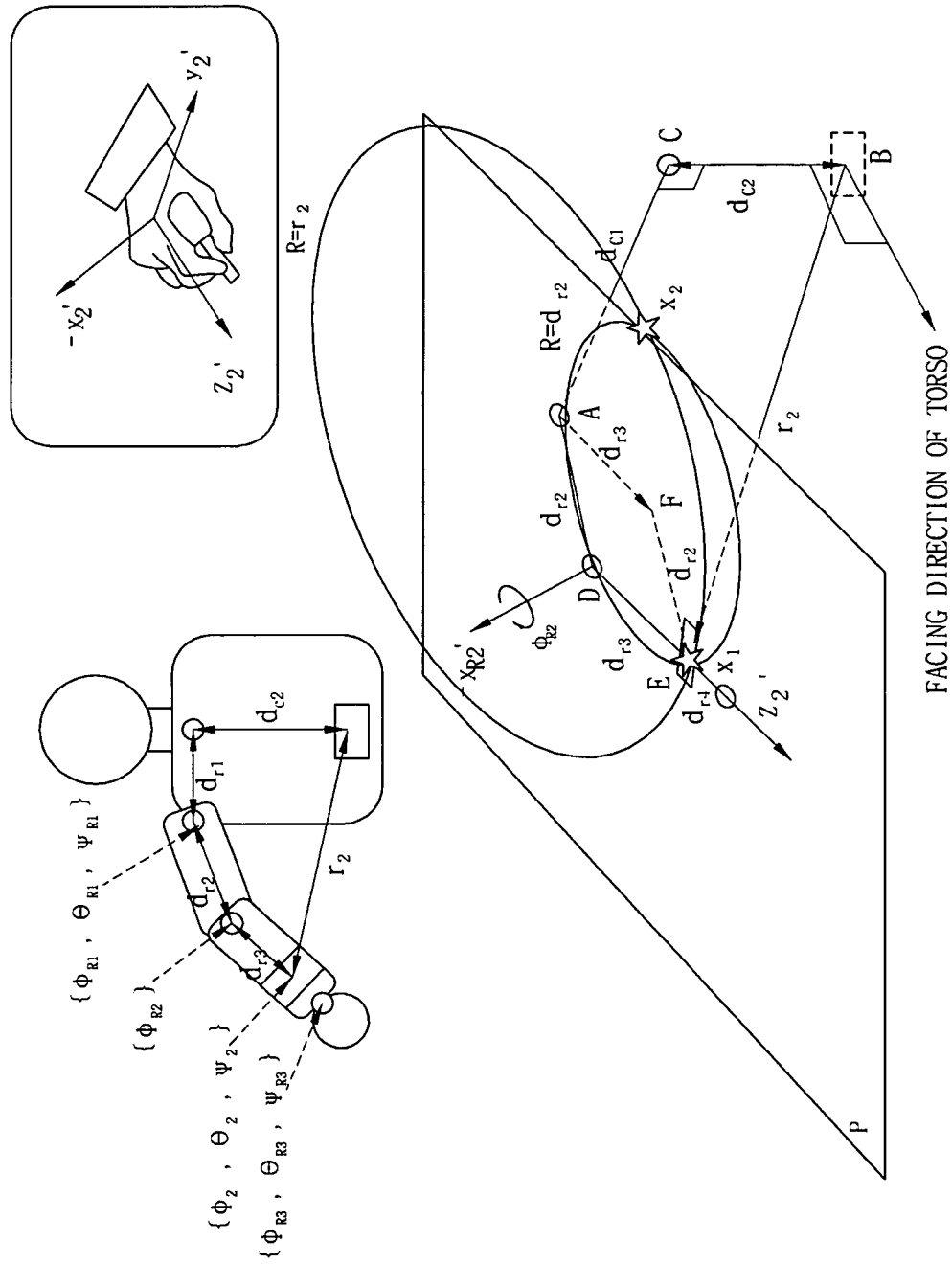
Figure 19:
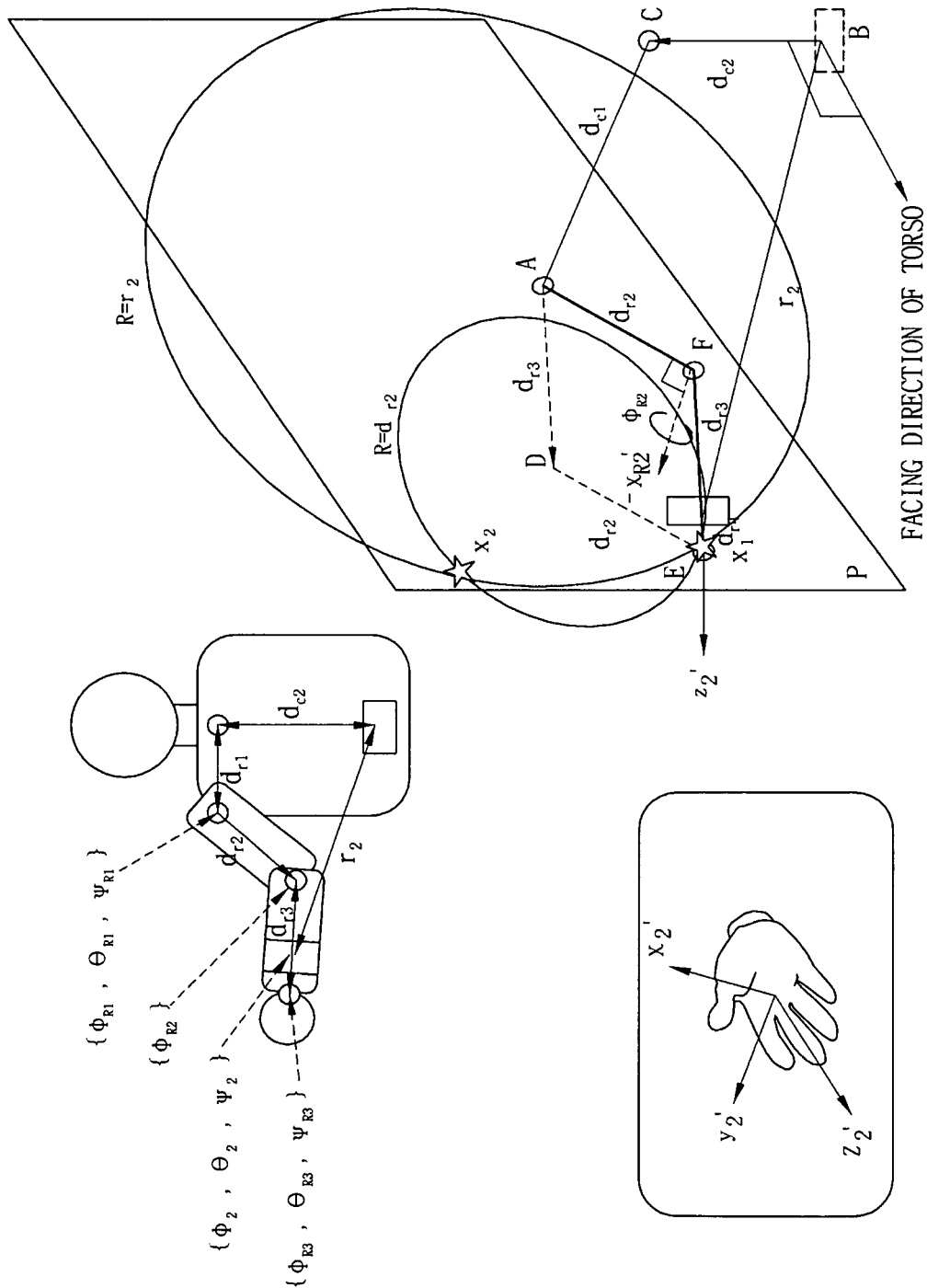
Figure 20:
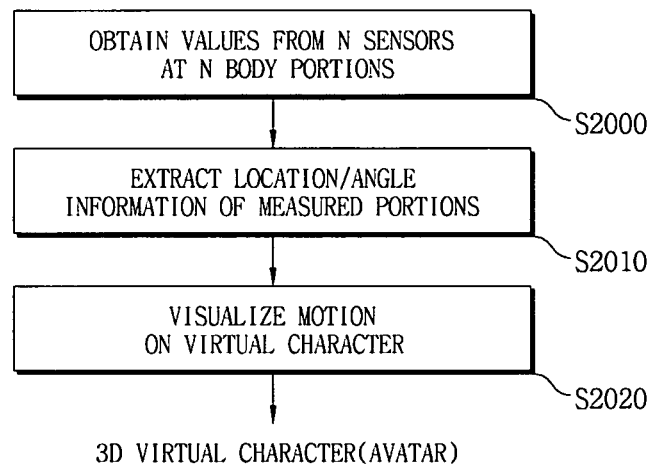
FIG. 20 illustrates a conventional method of capturing and demonstrating motion of an individual.

Therefore, the arm movements can be estimated as either of movements in FIG. 16, which will be explained in more detail with a corresponding discussion of FIG. 18, or movements in FIG. 17, which will be explained in more detail with a corresponding discussion of FIG. 19, for example. FIGS. 16-19 further illustrates such orientations of the palm relative to the remainder of the arm which controls such a determination of whether $\psi_{R3}$ is greater or less than 0.

FIG. 18 illustrates an explanation of how to estimate an arm movement when the rotation angle $\psi_{R3} \geq 0$, according to one or more embodiments.

Referring to FIG. 18, a half-line vector $\vec{AF}$ starts from a point A in a plane P, $Z_2'//\vec{AF}$. In this case, a point F which would enable the forming of a parallelogram rectangle ADEF in the plane may be determined, noting that F has the only value since $\angle ADE \leq \pi$. Moreover, in a skeleton model, $\overline{AC}$ and $\overline{BC}$ can be considered to have fixed length values $d_{r1}$ and $d_{c2}$, respectively as illustrated. A normal vector in a plane in which a triangle ABC lies may be determined through the aforementioned procedures, and hence the position and direction of F of $\vec{AF}$ can be determined with respect to a reference position B. To choose from among two potential orientations of the elbow of the arm, two spheres, one with a radius R of $d_{r2}$ from the point F and the other with a radius R of $r_2$ from the reference position B, may be compared; the two spheres may have two overlapping points $x_1$ and $x_2$. In this case, to ensure that the arm stretches out naturally, one of the points $x_1$ and $x_2$ may be selected, the selection being based on one of the points $x_1$ and $x_2$ whose AFX (=ADE) is greater. Then, since a position of E is determined from the measurement sensor and a direction vector of AF is already known, the position of D may be detected. Hence, the proper orientation of the joints of the right arm can be estimated.

FIG. 19 illustrates an explanation of how to estimate an arm movement when the rotation angle $\psi_{R3} \leq 0$ (for example, when the palm is up and the back of hand is turned downward away from the body), according to one or more embodiments.

Referring to FIG. 19, a half-line vector $\vec{AD}$ starts from a point A in a plane P, $Z_2'//\vec{AD}$. In this case, a point D which would enable the forming of a parallelogram rectangle ADEF in a plane may be determined, noting that F has the only value since AFE$\leq \pi$. Moreover, in a skeleton model, $\overline{AC}$ and $\overline{BC}$ can be considered to have fixed length values $d_{r1}$ and $d_{c2}$, respectively as illustrated. A normal vector in a plane in which a triangle ABC lies may be estimated through the aforementioned procedures, and hence the position and direction of D of $\vec{AD}$ can be estimated with respect to a reference position B.

To choose from among to potential orientations of the elbow of the arm, two spheres, one with a radius R of $d_{r2}$ from the point D and the other with a radius R of $r_2$ from the reference position B, may be compared; the two spheres may have two overlapping points $x_1$ and $x_2$. In this case, to ensure that the arm stretches out naturally, one of the points $x_1$ and $x_2$ may be selected, the selection being based on one of the points $x_1$ and $x_2$ whose ADX (=AFE) is greater. Then, since a position of E is determined from the measured sensor and a direction vector of AF is already known, the position of D may be detected. Hence, the proper orientation of the joints of the right arm can be determined.

In the above-described procedures for determining the movements of an arm, the reference sensor, generating the reference position, has been assumed to be placed at the navel or pelvis. That is, as noted above, such embodiments are based on the case where the reference position and the rotation center of the arm are far from each other. In comparison, similar to the above discussion for the leg, if the reference position is near the rotation center of the arm (for example, the reference position is at a chest or a shoulder), the movements of the arm may be estimated through procedures similar to the above-described procedures of estimating the movements of the leg.

Through the procedures described above, joint angles of a 3D virtual character are possibly estimated by given sensor information and joint angles, which are calculated based on appropriate assumptions of the degree of freedom for realization of movement.

In addition, a procedure may be additionally performed to realize more natural movements on an application platform. For example, in golf motions, the 3D virtual character grips a golf club, and folds a part of toes to look natural in a sitting position. Also, a virtual character of a fighting game may have a detailed set of movements to make a slight first while stretching the arm out straight in line with the characteristics of the character. Complicated movements of the virtual character may be sometimes hard for a human to conduct in real in terms of speed and motion and hence such the elaborated movements may be mapped into the standard movements of the virtual character to easily implement the same. Embodiments are equally not limited to such applications, but maybe available for alternative body movement estimation, such as through distant control for robotics or calibration of a control system for movement of a body. The estimated body movement is further not required to be applied to a 3D virtual character, but could be projected onto a 2D virtual character or not used to generate a virtual character at all, such as when the estimated movement information is used to control an interaction with a physical system, e.g., a robotic system or in a calibrating of a robotic system, noting that alternatives are equally available. The estimation data may further be available for an alternative interface with a computer for controlling the same or interacting with an application executed by the computer, such as an alternative to a keyboard or mouse interface for controlling the input of data or movement of a cursor.

Accordingly, in one or more embodiments, by defining the general movements and the detailed movements, the amount information need to be obtained from sensors may be minimized, and movements of a virtual character may be effectively created based on minimized information under the appropriate assumption of the human movements. Also, it is possible for created movements to be represented on an application platform by use of the hierarchical configuration of the movements.

In addition to the above described embodiments, embodiments can also be implemented through computer readable code/instructions in/on a medium, e.g., a computer readable medium, to control at least one processing device to implement any above described embodiment. The medium can correspond to any defined, measurable, and tangible structure permitting the storing and/or transmission of the computer readable code.

The computer readable code can be recorded included in/on a medium, such as a computer-readable media, and the computer readable code may include program instructions to implement various operations embodied by a processing device, such a processor or computer, for example. The media may also include, e.g., in combination with the computer readable code, data files, data structures, and the like. Examples of computer-readable media include magnetic media such as hard disks, floppy disks, and magnetic tape; optical media such as CD ROM disks and DVDs; magneto-optical media such as optical disks; and hardware devices that are specially configured to store and perform program instructions, such as read-only memory (ROM), random access memory (RAM), flash memory, and the like. Examples of computer readable code include both machine code, such as produced by a compiler, and files containing higher level code that may be executed by the computer using an interpreter, for example. The media may also be a distributed network, so that the computer readable code is stored and executed in a distributed fashion. Still further, as only an example, the processing element could include a processor or a computer processor, and processing elements may be distributed and/or included in a single device.

While aspects of the present invention has been particularly shown and described with reference to differing embodiments thereof, it should be understood that these exemplary embodiments should be considered in a descriptive sense only and not for purposes of limitation. Descriptions of features or aspects within each embodiment should typically be considered as available for other similar features or aspects in the remaining embodiments.

Thus, although a few embodiments have been shown and described, it would be appreciated by those skilled in the art that changes may be made in these embodiments without departing from the principles and spirit of the invention, the scope of which is defined in the claims and their equivalents.

What is claimed is:

1. A motion capture apparatus, comprising:
   an estimation unit to estimate posture information, including one or more rotation angles of plural portions of a body different from a portion of the body where a measurement sensor is positioned at, based on a detected distance representation and one or more of rotation angle measurements by the measurement sensor, according to the measurement sensor being positioned at the portion of the body and the measurement sensor measuring a distance representation between the measurement sensor and a reference position of a reference sensor positioned on or off the body, wherein, in the estimation of the posture information, posture estimation for the plural portions of the body is performed using a total number of measurement sensors that is less than a total corresponding number of joints of the plural portions of the body.

2. The motion capture apparatus of claim 1, wherein the plural portions of the body include another portion of the body having plural freedoms of motion, and wherein estimation of posture information for the other portion of the body is not based on measured posture information at the other portion of the body.

3. The motion capture apparatus of claim 2, wherein the portion of the body where the measurement sensor is positioned at has plural freedoms of motion.

4. The motion capture apparatus of claim 1, wherein the distance representation between the measurement sensor and the reference position defines a side of a triangle, with two other sides of the triangle being defined by two determined respective distances between portions of the body, and wherein the estimation unit estimates the posture information by defining at least one interior angle of the triangle.

5. The motion capture apparatus of claim 1, wherein, in the estimation of the posture information, the estimation unit defines a parallelogram, based on the distance representation between the measurement sensor and the reference position, to represent alternative positions of one of the plural portions, wherein sides of the parallelogram are defined by two determined respective distances between portions of the body.

6. A motion capture apparatus, comprising:
an estimation unit to estimate posture information, including one or more rotation angles of plural portions of a body different from a portion of the body where a measurement sensor is positioned at, based on a detected distance representation and one or more of rotation angle measurements by the measurement sensor, according to the measurement sensor being positioned at the portion of the body and detecting the distance representation between the measurement sensor and a reference position, wherein, in the estimation of the posture information, the estimation unit defines a parallelogram, based on the distance representation between the measurement sensor and the reference position, to represent alternative positions of one of the plural portions, wherein sides of the parallelogram are defined by two respective distances between portions of the body, and wherein the estimation unit selects one of the alternative positions of the one portion as a position of the one portion based on determined overlapping points of a first sphere having a radius of the distance representation and a second sphere having a radius of one of the two respective distances.

7. The motion capture apparatus of claim 1, wherein, in the estimation of the posture information, the estimation unit estimates the posture information by projecting into a plane one axis for one or more portions of the body and one axis of the portion of the body where the measurement sensor is positioned at to estimate posture information of the one or more portions of the body.

8. The motion capture apparatus of claim 1, wherein the motion capture apparatus comprises at least four measurement sensors, including the measurement sensor positioned at the portion of the body, positioned at different portions of the body detecting distance representations between respective measurement sensors and the reference position, and the estimation unit estimates posture information, including one or more rotation angles of plural portions of the body different from the different portions of the body where the at least four measurement sensors are positioned at, based on the detected distance representations and one or more of rotation angle measurements of the respective measurement sensors.

9. The motion capture apparatus of claim 1, further comprising the measurement sensor positioned at the portion of a body and to detect the distance representation between the measurement sensor and the reference position, wherein the measurement sensor includes an inertial sensor that obtains position and rotations angles of the portion of the body where the measurement sensor is positioned at based on detected inertial information from the inertial sensor.

10. The motion capture apparatus of claim 9, wherein the inertial sensor measures an acceleration along at least one axis and an angular velocity along at least one axis, with the inertial information including the measured acceleration and the measured angular velocity.

11. The motion capture apparatus of claim 1, wherein the posture information includes rotation angles and position coordinates of the plural portions of the body and the measurement sensor measures posture information of the portion of the body where the measurement sensor is positioned at.

12. The motion capture apparatus of claim 1, wherein the posture information of the body is estimated based on an interpretation of the body, including the plural portions of the body, as an articulation model set having a link structure.

13. The motion capture apparatus of claim 12, wherein a portion among from ends of the link, which is a center of joint movements, is defined as a rotation center and the estimation unit estimates the posture information in consideration of a distance between the rotation center and the reference position.

14. The motion capture apparatus of claim 1, wherein the estimation unit estimates the posture information by restricting a range of a rotation angle of a joint in consideration of a human behavioral pattern or by specifying a movement plane.

15. The motion capture apparatus of claim 1, wherein the body is a human body, and the motion capture apparatus further comprises measurement sensors, including the measurement sensor positioned at the portion of the body, positioned at each of a head, wrists, and ankles of the human body, the measurement sensors respectively detecting distance representations between each measurement sensor and the reference position, and wherein the estimation unit estimates posture information, including one or more rotation angles of the plural portions of the body different from rotation angle measurements of the measurement sensors, based on the detected distance representations by the measurement sensors and one or more rotation angles for each of the portions of the body measured by the measurement sensors.

16. The motion capture apparatus of claim 15, wherein at least one of the measurement sensors positioned at each of the wrists and ankles is attached to respective portions of the body physically adjacent to the respective wrists and ankles.

17. The motion capture apparatus of claim 1, wherein the reference position is a center portion of the body.

18. The motion capture apparatus of claim 1, wherein the body is a human body.

19. The motion capture apparatus of claim 1, wherein the plural portions are plural joint portions and the one or more rotation angle measurements are one or more joint rotation angle measurements.

20. The motion capture apparatus of claim 19, wherein the estimation unit is configured so that estimation of the one or more rotation angles of the plural joint portions of the body is enabled based on measurements from a number of measurement sensors less than a number of the plural joint portions whose posture information is estimated in the estimating of the posture information by the estimation unit.

21. The motion capture apparatus of claim 5, wherein the estimation unit selects one of the alternative positions of the one portion as a position of the one portion based on determined overlapping points of a first sphere having a radius of the distance representation and a second sphere having a radius of one of the two respective distances.

22. A motion capture apparatus, comprising:
an estimation unit to estimate posture information, including one or more rotation angles of plural portions of a body different from a portion of the body where a measurement sensor is positioned at, based on a detected distance representation and one or more of rotation angle measurements by the measurement sensor, according to the measurement sensor being positioned at the portion of the body and detecting the distance representation between the measurement sensor and a reference position;
the measurement sensor positioned at the portion of a body and to detect the distance representation between the measurement sensor and the reference position; and
a reference sensor to output reference position information, wherein the measurement sensor receives the output reference position information to detect the distance representation,
wherein, in the estimation of the posture information, posture estimation for the plural portions of the body is performed using a total number of measurement sensors that is less than a total corresponding number of joints of the plural portions of the body.

23. The motion capture apparatus of claim 22, wherein the reference sensor is positioned at the reference position.

24. The motion capture apparatus of claim 23, wherein the reference sensor is positioned on the body.

25. The motion capture apparatus of claim 24, wherein the reference sensor is positioned at a reference position portion of the body different from the portion of the body where the measurement sensor is positioned at and different from the plural portions of the body different from the portion of the body where the measurement sensor is positioned at.

26. The motion capture apparatus of claim 25, wherein the motion capture apparatus comprises at least four measurement sensors, including the measurement sensor positioned at the portion of the body, positioned at different portions of the body detecting distance representations between respective measurement sensors and the reference position, and
the estimation unit estimates posture information, including one or more rotation angles of plural portions of the body different from the different portions of the body where the at least four measurement sensors are positioned at, based on the detected distance representations and one or more of rotation angle measurements of the respective measurement sensors.

27. A motion capture method which maps movements of a body into a skeleton model for generating movements of a three-dimensional (3D) virtual character, the method comprising:

estimating posture information, including one or more rotation angles of plural portions of a body different from a portion of the body where a measurement sensor is positioned at, based on a detected distance representation and one or more of rotation angle measurements by the measurement sensor, according to the measurement sensor being positioned at the portion of the body and the measurement sensor measuring the distance between the measurement sensor and a reference position of a reference sensor positioned on or off the body,
wherein, in the estimating of the posture information, posture estimation for the plural portions of the body is performed using a total number of measurement sensors that is less than a total corresponding number of joints of the plural portions of the body.

28. The motion capture method of claim 27, wherein the plural portions of the body include another portion of the body having plural freedoms of motion, and wherein the estimating of posture information for the other portion of the body is not based on measured posture information by the other portion of the body.

29. The motion capture method of claim 28, wherein the portion of the body where the measurement sensor is positioned at has plural freedoms of motion.

30. The motion capture method of claim 27, wherein the distance representation between the measurement sensor and the reference position defines a side of a triangle, with two other sides of the triangle being defined by two determined respective distances between portions of the body, and wherein the estimating further comprises estimating the posture information by defining at least one interior angle of the triangle.

31. The motion capture method of claim 27, wherein, in the estimation of the posture information, the estimating further comprises defining a parallelogram, based on the distance representation between the measurement sensor and the reference position, to represent alternative positions of one of the plural portions, wherein sides of the parallelogram are defined by two respective determined distances between portions of the body.

32. The motion capture method of claim 27, wherein, in the estimating of the posture information, the estimating further comprises estimating the posture information by projecting into a plane one axis for one or more portions of the body and one axis of the portion of the body where the measurement sensor is positioned at to estimate posture information of the one or more portions of the body.

33. The motion capture method of claim 27, wherein the estimating further comprises estimating posture information, including one or more rotation angles of plural portions of the body different from different portions of the body where at least four measurement sensors are positioned at, based on detected distance representations respectively from the at least four measurement sensors and one or more of rotation angle measurements of the respective measurement sensors,
wherein the at least four measurement sensors include the measurement sensor positioned at the portion of the body.

34. The motion capture method of claim 27, further comprising:
generating a virtual character corresponding to the body by use of the one or more rotation angles and position coordinates of the plural portions of the body and the portion of the body where the measurement sensor is positioned at.

35. The motion capture method of claim 27, wherein the posture information of the body is estimated based on an interpretation of the body, including the plural portions of the body, as an articulation model set having a link structure.

36. The motion capture method of claim 35, wherein a portion among from ends of the link, which is a center of joint movements, is defined as a rotation center and the estimating further comprises estimating the posture information in consideration of a distance between the rotation center and the reference position.

37. The motion capture method of claim 35, wherein, in the estimating of the one or more rotation angles and an estimating of position coordinates, when the rotation center of the link structure is co-located with the reference position, a rotation angle of a joint having one degree of freedom is calculated before rotation angles of a joint having three degrees of freedom are calculated.

38. The motion capture method of claim 35, wherein, in the estimating of the one or more rotation angles and an estimating of position coordinates, when the rotation center of the link structure is not co-located with the reference position, candidates for a rotation angle and a rotation axis of a joint having one degree of freedom are estimated, a movement plane is set in consideration of a behavioral pattern of the body, and then rotation angles of previously unestimated joints are calculated.

39. The motion capture method of claim 27, wherein the one or more rotation angles and an estimating of position coordinates of the plural portions are restricted or a movement plane is determined according to situations in consideration of a human behavioral pattern in order to estimate one or more rotation angles and the position coordinates.

40. The motion capture method of claim 27, wherein the body is a human body,
wherein the estimating further comprises estimating posture information, including one or more rotation angles of the plural portions of the body different from rotation angle measurements of measurement sensors positioned at each of a head, wrists, and ankles portions of the body, based on detected distance representations by the measurement sensors, and one or more rotation angles for each portion of the body measured by the measurement sensors,
wherein the measurement sensors respectively detect the distance representations between each measurement sensor and the reference position.

41. The motion capture method of claim 40, wherein at least one of the measurement sensors positioned at each of the wrists and ankles is attached to respective portions of the body physically adjacent to the respective wrists and ankles.

42. The method of claim 27, wherein the reference position is at a center portion of the body or not on the body.

43. A non-transitory computer readable recording medium comprising computer readable code to control at least one processing device to implement the method of claim 27.

44. The method of claim 27, wherein the plural portions are plural joint portions and the one or more rotation angle measurements are one or more joint rotation angle measurements.

45. The method of claim 44, wherein estimation of the one or more rotation angles of the plural joint portions of the body includes enablement of the estimation of the one or more rotation angles of the plural joint portions of the body based on measurements from a number of measurement sensors less than a number of the plural joint portions when the number of measurement sensors is less than the number of the plural joint portions whose posture information is estimated in the estimating of the posture information.

46. The motion capture method of claim 31, wherein the estimating further comprises selecting one of the alternative positions of the one portion as a position of the one portion based on determined overlapping points of a first sphere having a radius of the distance representation and a second sphere having a radius of one of the two respective distances.

47. A motion capture method which maps movements of a body into a skeleton model for generating movements of a three-dimensional (3D) virtual character, the method comprising:
estimating posture information, including one or more rotation angles of plural portions of a body different from a portion of the body where a measurement sensor is positioned at, based on a detected distance representation and one or more of rotation angle measurements by the measurement sensor, according to the measurement sensor being positioned at the portion of the body and detecting the distance representation between the measurement sensor and a reference position,
wherein, in the estimation of the posture information, the estimating further comprises defining a parallelogram, based on the distance representation between the measurement sensor and the reference position, to represent alternative positions of one of the plural portions, wherein sides of the parallelogram are defined by two respective distances between portions of the body, and
wherein the estimating further comprises selecting one of the alternative positions of the one portion as a position of the one portion based on determined overlapping points of a first sphere having a radius of the distance representation and a second sphere having a radius of one of the two respective distances.

48. A motion capture method which maps movements of a body into a skeleton model for generating movements of a three-dimensional (3D) virtual character, the method comprising:
estimating posture information, including one or more rotation angles of plural portions of a body different from a portion of the body where a measurement sensor is positioned at, based on a detected distance representation and one or more of rotation angle measurements by the measurement sensor, according to the measurement sensor being positioned at the portion of the body and detecting the distance representation between the measurement sensor and a reference position; and
outputting reference position information, from a reference sensor, and the measurement sensor detecting the distance representation based on receipt of the reference position information,
wherein, in the estimating of the posture information, posture estimation for the plural portions of the body is performed using a total number of measurement sensors that is less than a total corresponding number of joints of the plural portions of the body.

49. The motion capture method of claim 48, wherein the reference sensor is positioned at the reference position.

50. The motion capture method of claim 49, wherein the reference sensor is positioned on the body.

51. The motion capture method of claim 50, wherein the reference sensor is positioned at a reference position portion of the body different from the portion of the body where the measurement sensor is positioned at and different from the plural portions of the body different from the portion of the body where the measurement sensor is positioned at.

52. The motion capture method of claim 51, wherein the estimating further comprises estimating posture information, including one or more rotation angles of plural portions of the body different from different portions of the body where at least four measurement sensors are positioned at, based on detected distance representations respectively from the at least four measurement sensors and one or more of rotation angle measurements of the respective measurement sensors,
wherein the at least four measurement sensors include the measurement sensor positioned at the portion of the body.

53. A motion capture apparatus, comprising:
an estimation unit which estimates posture information, including one or more rotation angles of non-extremity portions of a body based on one or more detected distance representations and rotation angle measurements measured by one or more measurement sensors, with the non-extremity portions including at least one of both an elbow and a shoulder and both a knee and a pelvis based on the one or more measurement sensors being positioned at a corresponding wrist area and/or ankle area of the body based on which non-extremity portions of the body posture information is being estimated by the estimation unit,
wherein the one or more measurement sensors are positioned only at respective different extremity portions of the body and respectively detect the one or more distance representations as between each measurement sensor and a reference position,
wherein, in the estimation of the posture information, posture estimation for the plural portions of the body is performed using a total number of measurement sensors that is less than a total corresponding number of joints of the plural portions of the body.

54. The motion capture apparatus of claim 53, further comprising the one or more measurement sensors to be positioned only at the different extremity portions of the body and to respectively detect the one or more distance representations.

55. A motion capture method, comprising:
estimating posture information, including one or more rotation angles of non-extremity portions of a body based on one or more detected distance representations and rotation angle measurements measured by one or more measurement sensors, with the non-extremity portions including at least one of both an elbow and a shoulder and both a knee and a pelvis based on the one or more measurement sensors being positioned at a corresponding wrist area and/or ankle area of the body based on which non-extremity portions of the body posture information is being estimated by the estimating,
wherein the one or more measurement sensors are positioned only at respective different extremity portions of the body and respectively detect the one or more distance representations as between each measurement sensor and a reference position,
wherein, in the estimating of the posture information, posture estimation for the plural portions of the body is performed using a total number of measurement sensors that is less than a total corresponding number of joints of the plural portions of the body.

56. The motion capture method of claim 55, further comprising detecting the one or more distance representations by the measurement sensors.

57. A non-transitory computer readable recording medium comprising computer readable code to control at least one processing device to implement the method of claim 55.

58. A motion capture apparatus, comprising:
an estimation unit to estimate posture information, including one or more rotation angles of plural portions of a body different from a portion of the body where a measurement sensor is positioned at, based on a detected distance representation and one or more of rotation angle measurements by the measurement sensor, according to the measurement sensor being positioned at the portion of the body and detecting the distance representation between the measurement sensor and a reference position,
wherein the plural portions are plural joint portions and the one or more rotation angle measurements are one or more joint rotation angle measurements, and
wherein the estimation unit is configured so that estimation, in the estimating of the posture information, of the one or more rotation angles of the plural joint portions of the body is enabled based on measurements from a total number of measurement sensors for the plural portions of the body less than a total number of the plural joint portions of the plural portions of the body.

59. A motion capture method which maps movements of a body into a skeleton model for generating movements of a three-dimensional (3D) virtual character, the method comprising:
estimating posture information, including one or more rotation angles of plural portions of a body different from a portion of the body where a measurement sensor is positioned at, based on a detected distance representation and one or more of rotation angle measurements by the measurement sensor, according to the measurement sensor being positioned at the portion of the body and detecting the distance representation between the measurement sensor and a reference position,
wherein the plural portions are plural joint portions and the one or more rotation angle measurements are one or more joint rotation angle measurements, and
wherein, in the estimating of the posture information, estimation of the one or more rotation angles of the plural joint portions of the body includes enablement of the estimation of the one or more rotation angles of the plural joint portions of the body based on measurements from a total number of measurement sensors for the plural portions of the body less than a total number of the plural joint portions of the plural portions of the body.

* * * * *